US012331339B2

United States Patent
Choi et al.

(10) Patent No.: US 12,331,339 B2
(45) Date of Patent: Jun. 17, 2025

(54) METHOD OF PRODUCING SULFUR-CONTAINING AMINO ACID OR DERIVATIVE THEREOF

(71) Applicant: CJ CHEILJEDANG CORPORATION, Seoul (KR)

(72) Inventors: Sol Choi, Seoul (KR); Hee Ju Kim, Seoul (KR); Jin Ah Rho, Seoul (KR); Jin Nam Lee, Seoul (KR); Han Hyoung Lee, Seoul (KR); Sun Young Lee, Seoul (KR); Sang Jun Kim, Seoul (KR); Jihyun Shim, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 657 days.

(21) Appl. No.: 17/597,007

(22) PCT Filed: Jun. 26, 2020

(86) PCT No.: PCT/KR2020/008415
§ 371 (c)(1),
(2) Date: Dec. 22, 2021

(87) PCT Pub. No.: WO2020/263043
PCT Pub. Date: Dec. 30, 2020

(65) Prior Publication Data
US 2022/0315963 A1    Oct. 6, 2022

(30) Foreign Application Priority Data

Jun. 28, 2019 (KR) .................. 10-2019-0077999

(51) Int. Cl.
  *C12P 13/12* (2006.01)
  *C07K 14/245* (2006.01)
  *C07K 14/34* (2006.01)
  *C12N 15/70* (2006.01)
  *C12N 15/77* (2006.01)
(52) U.S. Cl.
  CPC ............ *C12P 13/12* (2013.01); *C07K 14/245* (2013.01); *C07K 14/34* (2013.01); *C12N 15/70* (2013.01); *C12N 15/77* (2013.01)
(58) Field of Classification Search
  None
  See application file for complete search history.

(56) References Cited

U.S. PATENT DOCUMENTS

| 7,662,943 | B2 | 2/2010 | Park et al. |
| 8,148,117 | B2 | 4/2012 | Zelder et al. |
| 9,109,242 | B2 | 8/2015 | Park et al. |
| 10,273,491 | B2 | 4/2019 | Lee et al. |
| 10,584,338 | B2 | 3/2020 | Lee et al. |
| 2007/0026505 | A1 | 2/2007 | Madden et al. |
| 2009/0298135 | A1 | 12/2009 | Maier et al. |
| 2010/0317067 | A1 | 12/2010 | Kim et al. |
| 2013/0183726 | A1 | 7/2013 | Figge et al. |

FOREIGN PATENT DOCUMENTS

| JP | 2009-513119 A | 4/2009 |
| KR | 10-2007-0036139 A | 4/2007 |
| KR | 10-2008-0028940 A | 4/2008 |

OTHER PUBLICATIONS

Chica et al. Curr Opin Biotechnol. Aug. 2005; 16(4):378-84. (Year: 2005).*
Singh et al. Curr Protein Pept Sci. 2017, 18, 1-11 (Year: 2017).*
Accession Q8NR44. Oct. 1, 2002 (Year: 2002).*
Carpenter et al., 'Catalytic role of a conserved cysteine residue in the desulfonation reaction by the alkanesulfonate monooxygenase enzyme', Biochimica et Biophysica Acta, vol. 1804, No. 1, pp. 97-105 (2010).
Office Action received in Japanese Patent Application No. 577707/2021 dated Nov. 22, 2022 in 9 pages.
Eichhorn et al., J. Biol. Chem., vol. 274 (38), pp. 26639-26646 (1999).
Office Action in Korean Patent Application No. 10-2019-0077999 mailed on May 9, 2022.
Bolten, Christoph J., Hartwig Schroder, Jeroen Dickschat, and Christoph Wittmann. Towards Methionine Overproduction in Corynebacterium glutamicum Methanethiol and Dimethyldisulfide as Reduced Sulfur Sources. J. Microbiol. Biotechnol. (2010), 20(8), 1196-1203.
C. Troschel et al., "Characterization of Methionine Export in *Corynebacterium glutamicum*", Journal of Bacteriology, pp. 3786-3794, Jun. 2005.
D. J. Koch, C. Ruckert, D. A. Rey, A. Mix, A. Puhler, J. Kalinowski. 2005. Role of the ssu and seu Genes of Corynebacterium glutamicum ATCC 13032 in Utilization of Sulfonates and Sulfonate Esters as Sulfur Sources. AEM. 71.10.6104-6114. 2005.
Eichhorn, Eric et al., 'Deletion analysis of the *Escherichia coli* taurine and alkanesulfonate transport systems', Journal of Bacteriology, 2000, 182, 10, 2687-2795.
Rey et al., "The putative transcriptional repressor McbR, member of the TetR-family, is involved in the regulation of the metabolic network direting the synthesis of sulfur containing amino acids in *Corynebacterium glutamicum*", J. Biotechnol. 103:51-65, 2003.
J. Sambrook et al., Molecular Cloning, A Laboratory Manual, 2nd Edition, Cold Spring Harbor laboratory press, Cold Spring Harbor, New York, 1989.
Kertesz, Michael A., 'Bacterial transporters for sulfate and organosulfur compounds', Research in Microbiology, 2001, 152, 279-290.
Pearson et al. "Improved tools for biological sequence comparison", (1988) Proc. Natl. Acad. Sci. USA 85, pp. 2444-2448.

(Continued)

*Primary Examiner* — Christian L Fronda
(74) *Attorney, Agent, or Firm* — KNOBBE, MARTENS, OLSON & BEAR, LLP

(57) ABSTRACT

A method of producing sulfur-containing amino acids or derivatives of the sulfur-containing amino acids.

7 Claims, No Drawings
Specification includes a Sequence Listing.

(56) References Cited

OTHER PUBLICATIONS

Peyman, "Antisense Oligonucleotides: A New Therapeutic Principle", Chemical Reviews, 90:543-584 (1990).
Scheit, Nucleotide Analogs, John Wiley, New York (1980).
Sitnicka et al. Functional Analysis of Genes. Advances in Cell Biology. 2010, vol. 2.1-16, Sambrook et al. Molecular Cloning 2012, etc.
Van der Rest et al., "A heat shock following electroporation induces highly efficient transformation of *Corynebacterium glutamicum* with xenogeneic plasmid DNA", Appl Microbiol Biotechnol 52:541-545, 1999.
Extended European Search Report issued in European Patent Application No. 20830519.3, dated Aug. 19, 2022.
Eichhorn, Eric, Jan R. van der Ploeg, and Thomas Leisinger. "Characterization of a two-component alkanesulfonate monooxygenase from *Escherichia coli*." *Journal of Biological Chemistry* 274.38 (1999): 26639-26646.
Office Action received in Brazilian Office Action No. 1120210264868 dated Oct. 18, 2023.

\* cited by examiner

METHOD OF PRODUCING SULFUR-CONTAINING AMINO ACID OR DERIVATIVE THEREOF

CROSS-REFERENCE TO RELATED APPLICATIONS

This application is the U.S. National Phase under 35 U.S.C. § 371 of International Application PCT/KR2020/008415, filed Jun. 26, 2020, which was published in Korean as WO 2020/263043 on Dec. 30, 2020, which claims priority to Korean Patent Application No. 10-2019-0077999, filed Jun. 28, 2019 the entire content of which is incorporated herein by reference.

SEQUENCE LISTING STATEMENT

The present application contains a Sequence Listing, which is being submitted via EFS-Web on even date herewith. The Sequence Listing is submitted in a file entitled "Sequence_Listing_HAN030-011APC.txt," which was created on Dec. 22, 2021, and is approximately 39 kb in size. This Sequence Listing is hereby incorporated by reference.

TECHNICAL FIELD

The present disclosure relates to a method of producing a sulfur-containing amino acid or a derivative of the sulfur-containing amino acid.

BACKGROUND ART

L-Amino acids have been industrially produced by way of fermentation methods using microorganisms belonging to the genus *Brevibacterium*, the genus *Corynebacterium*, the genus *Escherichia*, and the like. In such production methods, bacterial strains isolated from nature, artificial mutant strains thereof, or strains modified to have enhanced activity of an enzyme involved in L-amino acid biosynthesis via DNA recombination technology have been used.

Meanwhile, sulfur-containing amino acids have been used as ingredients for synthesis of animal feeds, food additives, pharmaceutically injectable fluids, and medicaments, and research has been conducted to biologically produce sulfur-containing amino acids and derivatives thereof.

For example, U.S. Patent Application Publication No. US 2009-0298135 A1 discloses that 0.8 g/L of L-methionine was produced by deleting metJ gene on the genome of *Escherichia coli* and over-expressing YjeH protein, which is an L-methionine exporter. Also, BrnF and BrnE polypeptides have been reported as L-methionine exporters of *Corynebacterium glutamicum* (C. Troschel et al., *Journal of Bacteriology*, pp. 3786-3794, June 2005).

Meanwhile, in the production of sulfur-containing amino acids, an amount of NADPH consumed in microorganisms may vary according to the reducing power of a sulfur source. For example, while sulfides that do not require NADPH have the highest theoretical yields, sulfates that require four NADPHs have low theoretical yields. However, sulfides are disadvantageous in that they have been known to cause cell damage and have low stability. Therefore, a high yield may be expected in the case of using thiosulfate, which is a sulfur source having a low NADPH demand and high intracellular stability, in production of sulfur-containing amino acids. However, there has been no substantive research in efficiently utilizing thiosulfate in microorganisms of *Corynebacterium glutamicum*.

DISCLOSURE

Technical Problem

The present inventors have newly found that a protein encoded by ssuD gene is involved in utilizing thiosulfate and confirmed that a microorganism modified to have enhanced activity of the protein has enhanced ability to produce sulfur-containing amino acids using thiosulfate as a sulfur source, thereby completing the present disclosure.

Technical Solution

The present disclosure provides a method of producing a sulfur-containing amino acid and a derivative of the sulfur-containing amino acid, the method including culturing a genetically modified microorganism in a culture medium containing thiosulfate, wherein the microorganism includes genetic modification to increase activity of a protein encoded by ssuD gene compared to a non-modified microorganism.

The present disclosure provides a microorganism producing a sulfur-containing amino acid or a derivative of the sulfur-containing amino acid and including genetic modification to increase activity of a protein encoded by ssuD gene compared to a non-modified microorganism.

The present disclosure provides a composition for producing a sulfur-containing amino acid or a derivative of the sulfur-containing amino acid, wherein the composition includes: a microorganism including genetic modification to increase activity of a protein encoded by ssuD gene compared to a non-modified microorganism, or a culture thereof; and thiosulfate.

The present disclosure provides a use of a protein encoded by ssuD gene as a thiosulfate reductase.

The present disclosure provides a use of a microorganism including genetic modification to increase activity of a protein encoded by ssuD gene compared to a non-modified microorganism for producing a sulfur-containing amino acid or a derivative of the sulfur-containing amino acid.

Advantageous Effects

Sulfur-containing amino acids or derivatives thereof may be mass-produced using the microorganism, the composition, and the method of producing a sulfur-containing amino acid or a sulfur-containing amino acid thereof using the same according to the present disclosure, and thus may be efficiently used in production of useful products including the sulfur-containing amino acids or derivatives thereof.

BEST MODE

The present disclosure will be described in detail. Meanwhile, each description and embodiment disclosed in the present disclosure may be applied to different descriptions and embodiments herein. In other words, all combinations of various components disclosed in the present disclosure are included within the scope of the present disclosure. Furthermore, the scope of the present disclosure should not be limited by the descriptions provided below.

Those skilled in the art will recognize or be able to ascertain, using no more than routine experimentation, many equivalents to specific embodiments of the present disclosure. Such equivalents are intended to be encompassed in the scope of the present disclosure.

An aspect of the present disclosure provides a genetically modified microorganism producing a sulfur-containing amino acid or a derivative of the sulfur-containing amino acid.

Another aspect of the present disclosure provides a method of producing a sulfur-containing amino acid and a derivative of the sulfur-containing amino acid, the method including culturing a genetically modified microorganism in a culture medium containing thiosulfate.

The microorganism may include genetic modification to increase activity of a protein encoded by ssuD gene.

The present disclosure provides the method of producing a sulfur-containing amino acid and a derivative of the sulfur-containing amino acid, the method including culturing a genetically modified microorganism in a thiosulfate-containing culture medium, wherein the microorganism may include genetic modification to increase activity of a protein encoded by the ssuD gene compared to the microorganism before modification. In an embodiment of the present disclosure, the method may be a method of increasing production of sulfur-containing amino acids or derivatives of the sulfur-containing amino acids by the microorganism.

The manufacturing method may include bringing the microorganism having enhanced activity of the protein encoded by ssuD gene compared to intrinsic activity or a culture thereof into contact with thiosulfate.

As used herein, the expression "protein encoded by ssuD gene" refers to a protein that the ssuD gene encodes or a protein expressed by ssuD gene and may be referred to as "SsuD protein" (hereinafter, referred to as "SsuD protein"). Conventionally, SsuD protein has been known to be involved in degradation of sulfonate (R—SO$_3$), specifically as an alkanesulfonate monooxygenase, known as sulfonate monooxygenase. However, it is not known whether the SsuD protein is involved in utilizing thiosulfate rather than organic sulfate.

In the present disclosure, it has been newly revealed that the SsuD protein is involved in utilizing thiosulfate, specifically that it serves as a reductase that reduces thiosulfate, and it was confirmed that production of a sulfur-containing amino acid may be increased by enhancing the activity of the SsuD protein.

The SsuD protein of the present disclosure may be a protein encoded by ssuD gene and may be referred to as "SsuD protein", "thiosulfate reductase", or conventionally known "alkanesulfonate monooxygenase". In an embodiment, the SsuD protein of the present disclosure may be "sulfonate monooxygenase" or "thiosulfate reductase" derived from a microorganism belonging to the genus *Corynebacterium*, specifically a protein named LLM class flavin-dependent oxidoreductase derived from a microorganism belonging to the genus *Corynebacterium*. Specifically, the SsuD protein may be derived from *Corynebacterium glutamicum, Corynebacterium crudilactis, Corynebacterium deserti, Corynebacterium efficiens, Corynebacterium callunae, Corynebacterium stationis, Corynebacterium singulare, Corynebacterium halotolerans, Corynebacterium striatum, Corynebacterium ammoniagenes, Corynebacterium pollutisoli, Corynebacterium imitans, Corynebacterium testudinoris, Corynebacterium callunae, Corynebacterium crenatum, Corynebacterium deserti, Corynebacterium flavescens, Corynebacterium pacaense,* or *Corynebacterium suranareeae*, more specifically *Corynebacterium glutamicum*, without being limited thereto. An amino acid sequence of the SsuD protein may be available from a known database such as the National Center for Biotechnology Information (NCBI).

In an embodiment, the SsuD protein may include an amino acid sequence of SEQ ID NO: 43 or an amino acid sequence having at least 80%, 90%, 92%, 94%, 95%, 96%, 97%, 98%, or 99% homology or identity with the amino acid sequence of SEQ ID NO: 43. Also, it will be obvious that any protein having the amino acid sequence including deletion, modification, or addition of some amino acids is within the scope of the present disclosure as long as the amino acid sequence retains the above-described homology or identity and effects equivalents to those of the polypeptide.

In addition, any polypeptide, having sulfonate monooxygenase activity and thiosulfate-reducing activity and encoded by a polynucleotide hybridized with a probe constructed using known gene sequences, e.g., a nucleotide sequence entirely or partially complementary to the polynucleotide under stringent conditions, may also be included without limitation.

That is, in the present disclosure, although the expression "protein or polypeptide including an amino acid sequence of a predetermined SEQ ID NO", "protein or polypeptide consisting of an amino acid sequence of a predetermined SEQ ID NO", or "protein or polypeptide having an amino acid sequence of a predetermined SEQ ID NO" is used, it is obvious that any protein including deletion, modification, substitution, conservative substitution, or addition of one or several amino acids may be used in the present disclosure as long as the protein has activity identical or equivalent to that of the polypeptide consisting of the amino acid sequence of the SEQ ID NO. For example, addition of a sequence not changing the function of the protein to the N-terminus and/or the C-terminus of the amino acid sequence, a naturally occurring mutation, a silent mutation thereof, or a conservative substitution thereof may be used.

As used herein, the term "conservative substitution" refers to substitution of one amino acid with a different amino acid having similar structural and/or chemical properties. Such amino acid substitution may generally occur based on similarity of polarity, charge, solubility, hydrophobicity, hydrophilicity, and/or amphipathic nature of a residue.

In an embodiment of the present disclosure, the SsuD protein may be encoded by a polynucleotide having a nucleotide sequence of SEQ ID NO: 8, without being limited thereto.

As used herein, the term "polynucleotide" has an inclusive meaning including DNA and RNA molecules, and a nucleotide that is a basic structural unit in the polynucleotide may include not only a natural nucleotide but also an analogue in which a sugar or a base is modified (Scheit, *Nucleotide Analogs*, John Wiley, New York (1980); Uhlman and Peyman, *Chemical Reviews,* 90:543-584 (1990)).

The polynucleotide may be a polynucleotide (ssuD gene) encoding the SsuD protein of the present disclosure. The polynucleotide of the present disclosure may include various modifications made in a coding region provided not to change the amino acid sequence of the polypeptide expressed from the coding region due to codon degeneracy or in consideration of codons preferred by a living organism in which the protein is expressed. The polynucleotide of the present disclosure may be, for example, a polynucleotide encoding a polypeptide having at least 80%, 85%, 90%, 95%, 96%, 97%, 98%, 99%, or 100% homology or identity with the SsuD protein of the present disclosure. Specifically, the polynucleotide encoding a protein including an amino acid sequence having at least 80% homology or identity with the amino acid sequence of SEQ ID NO: 43 may be polynucleotides having at least 80%, 90%, 92%, 94%, 95%, 96%, 97%, 98%, or 99% homology or identity with the nucleotide sequence of SEQ ID NO: 8.

In addition, it is obvious that any polynucleotide that may be translated into a protein including an amino acid sequence having at least 80% homology or identity with SEQ ID NO: 43 due to codon degeneracy may be included. Alternatively, any polynucleotide encoding a protein including an amino acid sequence having at least 80% identity with the amino acid sequence of SEQ ID NO: 43 and hybridized with a probe constructed using known gene sequences, e.g., a nucleotide sequence entirely or partially complementary to the polynucleotide sequence under stringent conditions may be included without limitation. The term "stringent conditions" means conditions allowing specific hybridization between polynucleotides. Such conditions are disclosed in detail in known documents (For example, J. Sambrook et al., *Molecular Cloning, A Laboratory Manual*, 2nd Edition, Cold Spring Harbor Laboratory press, Cold Spring Harbor, New York, 1989; F. M. Ausubel et al., *Current Protocols in Molecular Biology*, John Wiley & Sons, Inc., New York). For example, the stringent conditions may include performing hybridization between genes having a high homology or identity, e.g., a homology or identity of 70% or more, 80% or more, 85% or more, specifically 90% or more, more specifically 95% or more, even more specifically 97% or more, or most specifically 99% or more, without performing hybridization between genes having a homology or identity lower than the above homologies or identities, or washing once, specifically twice or three times, under conventional washing conditions for Southern hybridization at a salt concentration and temperature of 60° C., 1×SSC, and 0.1% SDS, specifically 60° C., 0.1×SSC, 0.1% SDS, and more specifically 68° C., 0.1×SSC, and 0.1% SDS.

Hybridization requires that two polynucleotides have complementary sequences, although bases mismatch according to the degree of stringency of hybridization. The term "complementary" is used to describe the relationship between bases of nucleotides capable of hybridizing with each other. For example, with respect to DNA, adenosine is complementary to thymine and cytosine is complementary to guanine. Thus, the present disclosure may include not only a substantially similar nucleotide sequence but also a polynucleotide fragment isolated but complementary to the entire sequence.

Specifically, polynucleotides having homology or identity with the polynucleotide of the present disclosure may be detected using hybridization conditions including a hybridization process performed at a $T_m$ value of 55° C. and the above-described conditions. Also, the $T_m$ value may be, but is not limited to, 60° C., 63° C., or 65° C., and may be appropriately adjusted by those skilled in the art according to intended purposes.

An appropriate degree of stringency for hybridization of the polynucleotides may depend on lengths and a degree of complementarity of the polynucleotides and parameters thereof are well known in the art (Sambrook et al., supra, 9.50-9.51, 11.7-11.8).

As used herein, the term "homology" or "identity" refers to a degree of relatedness between two amino acid sequences or nucleotide sequences and may be expressed as a percentage. The terms homology and identity may often be used interchangeably.

Sequence homology or identity of conserved polynucleotides or polypeptides may be determined by standard alignment algorithm and default gap penalties established by a program may be used together therewith. Substantially, homologous or identical sequences may hybridize with each other at least about 50%, 60%, 70%, 80%, or 90% of the entire sequence or the entire length under moderate or highly stringent conditions. It is obvious that polynucleotides including a degenerate codon may also be considered in hybridization.

The homology, similarity, or identity between two polynucleotide or polypeptide sequences may be determined using any computer algorithm known in the art, e.g., "FASTA" program, using default parameters introduced by Pearson et al. (1988) *Proc. Natl. Acad. Sci. USA* 85:2444. Alternatively, the homology, similarity, or identity may be determined using the Needleman-Wunsch algorithm (Needleman and Wunsch, 1970, *J. Mol. Biol.* 48:443-453) as implemented in the Needleman program of the EMBOSS package (EMBOSS: The European Molecular Biology Open Software Suite, Rice et al., 2000, *Trends Genet.* 16:276-277) (version 5.0.0 or later) (including GCG program package (Devereux, J. et al., *Nucleic Acids Research* 12:387 (1984)), BLASTP, BLASTN, FASTA (Atschul, S. F., et al., *J MOLEC BIOL* 215:403 (1990); *Guide to Huge Computers*, Martin J. Bishop, ed., Academic Press, San Diego, 1994, and CARILLO et al. (1988) *SIAM J Applied Math* 48:1073). For example, the homology, similarity, or identity may be determined using BLAST, from the National Center for Biotechnology Information database, or ClustalW.

The homology, similarity, or identity between polynucleotides or polypeptides may be determined by comparing sequence information using a GAP computer program as introduced by Needleman et al., (1970), *J Mol Biol.* 48:443 as disclosed by Smith and Waterman, *Adv. Appl. Math* (1981) 2:482. Briefly, the GAP program defines similarity as the number of aligned symbols (i.e., nucleotides or amino acids) which are similar, divided by the total number of symbols in a shorter of two sequences. Default parameters for the GAP program may include: (1) a binary comparison matrix (containing a value of 1 for identities and 0 for non identifies) and the weighted comparison matrix of Gribskov et al. (1986), *Nucl. Acids Res.* 14:6745 as described by Schwartz and Dayhoff, eds., *Atlas Of Protein Sequence and Structure*, National Biomedical Research Foundation, pp. 353-358 (1979) (or EDNAFULL (EMBOSS version of NCBI NUC4.4) substitution matrix); (2) a penalty of 3.0 for each gap and an additional penalty of 0.10 for each symbol in each gap (or a gap open penalty of 10 and a gap extension penalty of 0.5); and (3) no penalty for end gaps.

Also, the sequence homology, similarity, or identity between two given polynucleotides or polypeptides may be identified by comparing sequences thereof by southern hybridization under defined stringent conditions, and the defined stringent hybridization conditions are within the scope of the technology and may be defined by a method well known to one of ordinary skill in the art (For example, J. Sambrook et al., *Molecular Cloning, A Laboratory Manual*, 2nd Edition, Cold Spring Harbor Laboratory press, Cold Spring Harbor, New York, 1989; F. M. Ausubel et al., *Current Protocols in Molecular Biology*, John Wiley & Sons, Inc., New York).

As used herein, the term "enhancement" of the activity of the polypeptide or protein refers to an increase in the activity of the polypeptide compared to intrinsic activity. The enhancement may be used interchangeably with up-regulation, overexpression, increase, and the like.

In this regard, the increase may include all of those exhibiting activity that was not originally possessed or exhibiting enhanced activity compared to intrinsic activity or activity before modification. The "intrinsic activity"

refers to activity of a particular polypeptide or protein originally possessed by a parent strain or non-modified microorganism before transformation when the microorganism is transformed by genetic modification caused by a natural or artificial factor. This term may be used interchangeably with "activity before modification". The "enhancement" or "increase" of activity of a polypeptide or protein compared to intrinsic activity means that activity of a particular polypeptide or protein is improved compared to that originally possessed by a parent strain or non-modified microorganism before transformation.

The term "increase in activity" may be achieved by introduction of a foreign polypeptide or protein or enhancement of activity of an endogenous polypeptide or protein, specifically achieved by enhancement of activity of an endogenous polypeptide or protein. The enhancement of activity of the polypeptide or protein may be identified based on an increase in a degree of activity of the polypeptide or protein, an expression level thereof, or an amount of a product released therefrom.

As used herein, the expression "enhancement or increase of activity of a protein encoded by ssuD gene or SsuD protein" may also be referred to as "genetic modification to increase activity of a protein encoded by ssuD gene", and this means that the activity of the protein is enhanced compared to intrinsic activity.

The increase in activity of the SsuD protein may include both an increase in the activity by introduction of a foreign SsuD protein and an increase in activity of endogenous SsuD protein.

As used herein, the term "introduction of a protein" refers to providing activity of a particular protein to a microorganism which does not originally possess the protein or enhancing the activity of the protein compared to the intrinsic activity of the protein or the activity before modification. For example, the introduction of a protein may refer to introduction of a particular protein, introduction of a polynucleotide encoding a particular protein into a chromosome of the microorganism, or introduction of a vector including a polynucleotide encoding a particular protein into a microorganism, thereby expressing the activity of the protein.

Enhancement of the activity of the polypeptide or protein may be achieved by applying various methods well known in the art without limitation, as long as the activity of a target polypeptide or protein is enhanced compared to that of the microorganism before modification. Specifically, any genetic engineering and/or protein engineering methods well known in the art as common methods of the molecular biology may be used, without being limited thereto (Sitnicka et al. Functional Analysis of Genes. *Advances in Cell Biology.* 2010, Vol. 2.1-16, Sambrook et al. *Molecular Cloning* 2012, etc.).

Specifically, in the present disclosure, the enhancement of the activity may be achieved by:
  (1) increasing a copy number of a gene or polynucleotide encoding the polypeptide or protein in a cell;
  (2) replacing a gene expression regulatory region on the chromosome encoding the polypeptide or protein with a sequence with stronger activity;
  (3) modifying a base sequence encoding an initiation codon or a 5'-UTR region of the polypeptide or protein;
  (4) modifying a nucleotide sequence on the chromosome to enhance the activity of the polypeptide or protein;
  (5) introducing a foreign polynucleotide having the activity of the polypeptide or protein or a codon optimized variant polynucleotide of the polynucleotide; or
  (6) modification to enhance the activity via any combination of the above-described methods, without being limited thereto.

The method of enhancing activity of a polypeptide or protein by the protein engineering method may be performed by modifying or chemically modifying an exposed region selected by analyzing a three-dimensional structure of the polypeptide or protein, without being limited thereto.

The increasing of the copy number of the gene or polynucleotide encoding the polypeptide or protein described in (1) above may be performed by any method well known in the art, e.g., by introducing a vector, which replicates and functions irrespective of a host cell and is operably linked to the gene or polynucleotide encoding the polypeptide or protein, into a host cell. Alternatively, the increasing of the copy number may be performed by introducing a vector, which is operably linked to the gene and is capable of inserting the gene or polynucleotide into the chromosome of the host cell, into the host cell, but is not limited thereto.

The replacing of the gene expression regulatory region (or expression regulatory sequence) on the chromosome encoding the polypeptide or protein with a sequence with stronger activity described in (2) above may be performed by any method known in the art, e.g., by inducing mutation in the sequence by deletion, insertion, non-conservative or conservative substitution, or any combination thereof or by replacing the sequence with a sequence with stronger activity, to further enhance the activity of the expression regulatory region. The expression regulatory region may include a promoter, an operator sequence, a ribosome-binding site-encoding sequence, and a sequence for regulating termination of transcription and translation, without being limited thereto. For example, the method may be performed by linking a stronger heterologous promoter instead of an intrinsic promoter, without being limited thereto.

Examples of the stronger promoter known in the art may include cj1 to cj7 promoters (U.S. Pat. No. 7,662,943 B2), lac promoter, trp promoter, trc promoter, tac promoter, Lambda phage PR promoter, PL promoter, tet promoter, lysCP1 promoter (US 2010-0317067 A1), spl1 promoter, sp17 promoter, sp113 promoter (U.S. Ser. No. 10/584,338 B2), gapA promoter, EF-Tu promoter, groEL promoter, aceA or aceB promoter, O2 promoter (U.S. patent Ser. No. 10/273,491 B2), tkt promoter, and yccA promoter, without being limited thereto.

The modifying of the base sequence encoding an initiation codon or a 5'-UTR region of the polypeptide or protein described in (3) above may be performed by any method known in the art, e.g., by substituting an intrinsic initiation codon with another initiation codon with a higher expression level of the polypeptide or protein, without being limited thereto.

The modifying the nucleotide sequence on the chromosome to enhance the activity of the polypeptide or protein described in (4) above may be performed by any method known in the art, e.g., by inducing modification on an expression regulatory sequence by deletion, insertion, non-conservative or conservative substitution, or any combination thereof to further enhance the activity of the nucleotide sequence or replacing the sequence with a nucleotide sequence modified to have stronger activity. The replacing may be insertion of the gene into the chromosome by homologous recombination, without being limited thereto. A vector used herein may further include a selection marker to detect the chromosomal insertion.

The introducing of the foreign polynucleotide having the activity of the polypeptide or protein described in (5) above may be performed by any method known in the art, e.g., by introducing a foreign polynucleotide encoding a polypeptide or protein having activity identical/similar to that of the polypeptide or protein, or introducing a codon optimized variant polynucleotide thereof into a host cell. The origin or sequence of the foreign polynucleotide is not particularly limited as long as the foreign polynucleotide exhibits activity identical/similar to that of the polypeptide or protein. In addition, a foreign polynucleotide codon-optimized for optimized transcription and translation in the host cell may be introduced into the host cell. The introduction may be performed by any known transformation method appropriately selected by those of ordinary skill in the art. As the introduced polynucleotide is expressed in the host cell, the polypeptide or protein is produced, thereby increasing the activity thereof.

Finally, the combination of the above-described methods described in (6) may be performed by applying one or more methods described in (1) to (5).

The enhancement of the activity of the polypeptide or protein as described above may be an increase in the activity or concentration of the polypeptide or protein compared with the activity or concentration of the polypeptide or protein expressed in wild-type or non-modified microorganism strains or an increase in an amount of a product obtained from the polypeptide or protein, without being limited thereto.

As used herein, the term "strain before modification" or "microorganism before modification" does not exclude strains including mutations naturally occurring in microorganisms and may refer to a wild-type strain or natural-type strain, or a strain before being transformed by genetic modification due to a natural or artificial factor. The "strain before modification" or "microorganism before modification" may be used interchangeably with "non-mutated strain", "non-modified strain", "non-mutated microorganism", "non-modified microorganism", or "reference microorganism".

As used herein, the term "vector" refers to a DNA construct containing a nucleotide sequence of a polynucleotide encoding a target protein and operably linked to a suitable regulatory sequence so as to be able to express the target protein in a suitable host cell. The regulatory sequence may include a promoter capable of initiating transcription, any operator sequence for regulating the transcription, a sequence encoding a suitable mRNA ribosome binding site, and a sequence for regulating termination of transcription and translation. When a suitable host cell is transformed with the vector, the vector may replicate or function independently from the host genome, or may integrate into genome thereof. For example, a polynucleotide encoding a target protein may be inserted into the chromosome by using a vector for chromosomal insertion into cells. The insertion of the polynucleotide into the chromosome may be performed by any method known in the art, for example, homologous recombination, but is not limited thereto. The vector may further include a selection marker to detect chromosomal insertion. The selection marker is used to select cells that are transformed with the vector, that is, to confirm insertion of desired nucleic acid molecules, and examples of the selection marker may include markers providing selectable phenotypes, such as drug tolerance, nutrient requirement, resistance to cytotoxic agents, or expression of surface polypeptide. Only cells expressing the selection marker are able to survive or to show different phenotypes under the environment treated with a selective agent, and thus the transformed cells may be selected.

The vector used in the present disclosure is not particularly limited, and any vector known in the art may be used. Examples of vectors commonly used in the art may include a natural or recombinant plasmid, cosmid, virus and bacteriophage. For example, pWE15, M13, MBL3, MBL4, IXII, ASHII, APII, t10, t11, Charon4A, and Charon21A may be used as the phage vector or the cosmid vector. As the plasmid vector, pBR type, pUC type, pBluescriptII type, pGEM type, pTZ type, pCL type, and pET type may be used. Specifically, pDZ, pACYC177, pACYC184, pCL, pECCG117, pUC19, pBR322, pMW118, and pCC1 BAC may be used. However, the embodiment is not limited thereto.

As used herein, the term "transformation" refers to a process of introducing a vector including a polynucleotide encoding a target protein into a host cell or microorganism in such a way that the polypeptide encoded by the polynucleotide is expressed in the host cell. The transformed polynucleotide may be either in a form inserted into the chromosome of the host cell or in a form located outside the chromosome as long as the protein is expressed in the host cell. In addition, the polynucleotide includes DNA and/or RNA encoding the target protein. The polynucleotide may be introduced into the host cell in any form as long as the polynucleotide is introduced into the host cell and the polypeptide is expressed therein. For example, the polynucleotide may be introduced into the host cell in the form of an expression cassette that is a gene construct including all of the essential elements required for self-replication. The expression cassette may generally include a promoter operably linked to the polynucleotide, a transcription termination signal, a ribosome-binding site, and a translation termination signal. The expression cassette may be in the form of a self-replicable expression vector. Also, the polynucleotide may be introduced into the host cell in its original form and operably linked to a sequence required for the expression in the host cell, without being limited thereto.

In addition, as used herein, the term "operably linked" refers to an operable linkage between a promoter sequence, which enables initiation and mediation of transcription of a polynucleotide encoding the target protein of the present disclosure, and the gene sequence.

Methods for the transformation with the vector according to the present disclosure include any methods enabling introduction of a nucleic acid into a host cell and may be performed by suitable standard techniques well known in the art selected in accordance with the host cell. For example, electroporation, calcium phosphate ($CaPO_4$) precipitation, calcium chloride ($CaCl_2$) precipitation, microinjection, polyethylene glycol (PEG) method, DEAE—dextran method, cationic liposome method, and lithium acetate—DMSO method may be used, but the present disclosure is not limited thereto.

The microorganism of the present disclosure may include both wild-type microorganisms and microorganisms including natural or artificial genetic modification, and any microorganism introduced with or including a thiosulfate reductase according to the present disclosure may be included therein without limitation.

The microorganism of the present disclosure may include: at least one of the thiosulfate reductase of the present disclosure; a polynucleotide encoding the same; and a vector including the polynucleotide.

The microorganism may be a microorganism producing L-amino acids and/or derivatives thereof.

As used herein, the term "microorganism producing L-amino acids and/or derivatives thereof" includes both a microorganism naturally having the ability to produce L-amino acids/derivatives thereof and a microorganism prepared by providing the ability to produce L-amino acids/derivatives thereof to a parent strain unable to produce the L-amino acids or derivatives thereof. Specifically, any microorganism including genetic modification to produce a target L-amino acid or derivatives thereof by having a particular mechanism weakened or enhanced via introduction of an exogenous gene or enhancement or inactivation of activity of an endogenous gene.

For example, the microorganism may be a microorganism in which a biosynthesis pathway of an L-amino acid is enhanced or a degradation pathway thereof is weakened. For example, the microorganism may be a microorganism in which an L-methionine biosynthesis pathway is enhanced.

For example, the microorganism may be a microorganism in which activity of methionine and cysteine biosynthesis repressor (McbR) protein or MetJ protein is weakened or eliminated or a microorganism in which the methionine producing ability is enhanced and/or added by enhancing activity of methionine synthase (MetH) or sulfite reductase (CysI). Alternatively, the microorganism may be a microorganism in which expression of a gene encoding an enzyme involved in the L-amino acid biosynthesis pathway is enhanced or an enzyme involved in the L-amino acid degradation pathway is weakened/inactivated.

Specifically, examples of proteins or genes whose expression may be controlled to enhance the biosynthesis pathway of L-amino acids or weaken/inactivate the degradation pathway thereof are as follows. They are provided in the order of a protein, a representative gene encoding the protein, and a representative EC number thereof. A first letter of the protein is written by a capital letter and the gene is written using italic font. For example, thiosulfate sulfurtransferase such as Rdl2p, GlpE, PspE, YgaP, ThiI, YbbB, SseA, YnjE, YceA, YibN, NCgl0671, NCgl1369, NCgl2616, NCgl0053, NCgl0054, NCGl2678, and NCgl2890; sulfite reductase, cysI; thiosulfate/sulphate transport system, cysPUWA (EC 3.6.3.25); 3'-phosphoadenosine 5'-phosphosulphate reductase, cysH (EC 1.8.4.8); sulfite reductase, cysJI (EC 1.8.1.2); cysteine synthase A, cysK (EC 2.5.1.47); cysteine synthase B, cysM (EC 2.5.1.47); serine acetyltransferase, cysE (EC 2.3.1.30); glycine cleavage system, gcvTHP-lpd (EC 2.1.2.10, EC 1.4.4.2, EC 1.8.1.4); lipoyl synthase, lipA (EC 2.8.1.8); lipoyl protein ligase, lipB (EC 2.3.1.181); phosphoglycerate dehydrogenase, serA (EC 1.1.1.95); 3-phosphoserine phosphatase, serB (EC 3.1.3.3); 3-phosphoserine/phosphohydroxythreonine aminotransferase, serC (EC 2.6.1.52); serine hydroxymethyltransferase, glyA (EC 2.1.2.1); aspartokinase I (EC 2.7.2.4); homoserine dehydrogenase I, thrA (EC 1.1.1.3); aspartate kinase, lysC (EC 2.7.2.4); homoserine dehydrogenase, hom (EC 1.1.1.3); homoserine O-acetyltransferase, metX (EC 2.3.1.31); homoserine O-succinyltransferase, metA (EC 2.3.1.46); cystathionine gamma-synthase, metB (EC 2.5.1.48); β-C-S-lyase, aecD (EC 4.4.1.8, beta-lyase); cystathionine beta-lyase, metC (EC 4.4.1.8); B12-independent homocysteine S-methyltransferase, metE (EC 2.1.1.14); methionine synthase, metH (EC 2.1.1.13); methylenetetrahydrofolate reductase, metF (EC 1.5.1.20); L-methionine exporter BrnFE; valine exporter YgaZH (B2682, B2683), ygaZH (b2682, b2683); exporter YjeH, b4141; pyridine nucleotide transhydrogenase PntAB, pntAB (EC 1.6.1.2); O-succinylhomoserine sulfhydrylase, MetZ (EC 2.5.1.48); and phosphoenolpyruvate carboxylase, Pyc (EC 4.1.1.31) may be used. The biosynthesis pathway of L-amino acids may be enhanced, or the degradation pathway thereof may be weakened by enhancing the activity of one or more proteins described above or some proteins constituting the system or by overexpressing polynucleotides encoding the same. Alternatively, among glucose 6-phosphate isomerase, pgi (EC 5.3.1.9); homoserine kinase, thrB (EC 2.7.1.39); S-adenosylmethionine synthase, metK (EC 2.5.1.6); dihydrodipicolinate synthase, dapA (EC 4.2.1.52); phosphoenolpyruvate carboxylkinase, pck (EC 4.1.1.49); formyltetrahydrofolate hydrolase, purU (EC 3.5.1.10); pyruvate kinase I, pykF (EC 2.7.1.40); pyruvate kinase II, pykA (EC 2.7.1.40); cystathionine γ-lyase, cg3086 (EC 4.4.1.1); cystathionine β-synthase, cg2344 (EC 4.2.1.22); regulatory protein Cg3031, cg3031; methionine and cysteine biosynthesis repressor protein McbR, mcbR; Met transcriptional repressor protein, metJ; L-methionine transporter MetQNI, metQ, metN, metI; N-acyltransferase, yncA; sRNA fnrS; and L-methionine transporter, metP, at least one protein selected therefrom may be inactivated or weakened or expression of the gene encoding the protein may be suppressed or removed.

However, these are merely examples, and the microorganism may be a microorganism in which expression of a gene encoding an enzyme involved in various known L-amino acid biosynthesis pathways is enhanced or an enzyme involved in degradation pathways are weakened/inactivated, without being limited thereto. The L-amino acid-producing microorganism may be prepared by way of various methods known in the art. The enhancement of activity of protein and increase in gene expression are as described above.

As used herein, the term "inactivation" or "weakening" of a polypeptide or protein is a concept including both reduction and elimination of the activity compared to intrinsic activity. The inactivation or weakening may be used interchangeably with down-regulation, decrease, and reduce. The inactivation or weakening may include a case in which activity of the protein is reduced or eliminated compared to intrinsic activity of the microorganism by mutation of a gene encoding the protein, modification of an expression regulatory sequence, or deletion of the gene in whole or in part, a case in which the overall activity of the protein in a cell is lower than that of native strains or non-modified strains due to inhibition of expression or translation of the gene encoding the same, a case in which the gene is not expressed, and a case in which no activity is obtained although the gene is expressed.

In the present disclosure, the inactivation/weakening of a protein may be achieved by various methods well known in the art, without being limited thereto (Nakashima N. et al., Bacterial cellular engineering by genome editing and gene silencing. *Int J Mol Sci.* 2014; 15(2):2773-2793, Sambrook et al. *Molecular Cloning* 2012, etc.).

Examples of the methods include
(1) deletion of the gene encoding the protein in whole or in part,
(2) modification of an expression regulatory region (or expression regulatory sequence) to reduce expression of the gene encoding the protein,
(3) modification of the gene sequence encoding the protein to eliminate or weaken the activity of the protein,
(4) introduction of an antisense oligonucleotide (e.g., introduction of antisense RNA) complementarily binding to a gene transcript encoding the protein,
(5) addition of a sequence complementary to a Shine-Dalgarno sequence of the gene encoding the protein upstream of the Shine-Dalgarno sequence to form a secondary structure preventing a ribosome from binding thereto, (6) addition of a promotor for reverse transcription to the 3' terminus of the open reading frame (ORF) of a nucleotide sequence of the gene encoding the protein (Reverse transcription engineering, RTE), or any combination thereof, without being limited thereto.

Specifically, the deletion of the gene encoding the protein in whole or in part may be performed by replacing a polynucleotide encoding an intrinsic target protein in the chromosome with a polynucleotide having some deleted nucleotides or a marker gene using a vector for chromosomal insertion in the microorganism. As an example of deleting the polynucleotide in whole or in part, a method of deleting the polynucleotide by homologous recombination may be used, without being limited thereto.

In addition, the deletion of the gene in whole or in part may be performed by inducing mutation using light such as UV light or a chemical substance, and selecting strains from which the target gene is deleted from mutants. The deletion of the gene may include a method by DNA recombination technology. The DNA recombination technology may be performed by inducing homologous recombination by inserting a nucleotide sequence or vector having homology with the target gene into the microorganism. In addition, the inserted nucleotide sequence or vector may include a dominant selection marker, without being limited thereto.

In addition, the modification of the expression regulatory sequence may be achieved by applying various methods well known in the art. For example, the modification may be performed by inducing mutation in the expression regulatory region (expression regulatory sequence) by deletion, insertion, non-conservative or conservative substitution, or any combination thereof to further reduce the activity of the expression regulatory region (expression regulatory sequence) or by replacing the sequence with a sequence having weaker activity. The expression regulatory region may include a promoter, an operator sequence, a ribosome-binding site-encoding sequence, and a sequence for regulating termination of transcription and translation, without being limited thereto.

Also, the modification of the gene sequence may be performed by inducing mutation in the gene sequence by deletion, insertion, non-conservative or conservative substitution, or any combination thereof to further weaken the activity of the polypeptide or by replacing the sequence with a gene sequence modified to have weaker activity or a gene sequence modified not to have the activity, without being limited thereto.

For example, expression of the gene may be suppressed or weakened by forming a termination codon by introducing a mutation into the gene sequence.

However, the above-described methods are merely examples and those of ordinary skill in that art may prepare a microorganism producing L-amino acids and/or derivatives thereof using any method known in the art.

The L-amino acid and/or a derivative thereof may be a sulfur-containing amino acid and/or a derivative of the sulfur-containing amino acid.

As used herein, the term "sulfur-containing amino acid" or "derivative of the sulfur-containing amino acid" refers to an amino acid including sulfur or a derivative thereof, specifically one selected from methionine, cysteine, cystine, lanthionine, homocysteine, homocystine, homolanthionine, and taurine, but is not limited thereto, any amino acid including sulfur and derivatives thereof may be included within the scope of the present disclosure without limitation.

The microorganism of the present disclosure may be a microorganism belonging to the genus *Corynebacterium* sp., the genus *Escherichia* sp., or the genus *Lactobacillus* sp., without being limited thereto. The microorganism may include any microorganism having enhanced ability to produce L-amino acids and/or derivatives thereof by enhancing intrinsic activity of SsuD protein or introducing a foreign SsuD protein, without limitation.

The "microorganism belonging to the genus *Corynebacterium*" may include all microorganisms belonging to the genus *Corynebacterium*. Specifically, the microorganism may be *Corynebacterium glutamicum*, *Corynebacterium crudilactis*, *Corynebacterium crenatum*, *Corynebacterium deserti*, *Corynebacterium efficiens*, *Corynebacterium callunae*, *Corynebacterium stationis*, *Corynebacterium singulare*, *Corynebacterium halotolerans*, *Corynebacterium striatum*, *Corynebacterium ammoniagenes*, *Corynebacterium pollutisoli*, *Corynebacterium imitans*, *Corynebacterium testudinoris*, or *Corynebacterium flavescens*, and more specifically *Corynebacterium glutamicum*, *Corynebacterium callunae*, *Corynebacterium crenatum*, *Corynebacterium stationis*, *Corynebacterium ammoniagenes*, or *Corynebacterium deserti*, even more specifically *Corynebacterium glutamicum*, but is not limited thereto.

The "microorganism belonging to the genus *Escherichia*" may include all microorganisms belonging to the genus *Escherichia*. Specifically, the microorganism may be *Escherichia coli*, but is not limited thereto.

The microorganism of the present disclosure may be any microorganism including the thiosulfate reductase of the present disclosure and using thiosulfate as a sulfur source.

The production method of the present disclosure may include culturing the microorganism of the present disclosure in a culture medium containing thiosulfate.

As used herein, the term "culturing" refers to growing the microorganism in an appropriately adjusted environment. A culture process of the present disclosure may be performed according to an appropriate medium and culturing conditions known in the art. The culture process may be easily adjusted for use by a skilled person in the art according to a strain to be selected. The culturing of the microorganism may be performed in in a batch process, a continuous process, a fed-batch process, etc. known in the art, without being limited thereto.

As used herein, the term "culture medium" refers to a material in which nutrients required for culturing the microorganism are mixed as main ingredients and supplies nutrients and growth factors as well as water which are essential for survival and growth. Specifically, although culture media and other culturing conditions for culturing the microorganism of the present disclosure are not particularly limited as long as the culture media are commonly used in culturing microorganisms, the microorganism of the present disclosure may be cultured in an ordinary medium containing appropriate carbon sources, nitrogen sources, phosphorus sources, inorganic compounds, amino acids, and/or vitamins under aerobic conditions while adjusting temperature, pH, and the like.

In the present disclosure, the carbon sources may include carbohydrates such as glucose, saccharose, lactose, fructose, sucrose and maltose; sugar alcohols such as mannitol and sorbitol; organic acids such as pyruvic acid, lactic acid, and citric acid; and amino acids such as glutamic acid, methionine, and lysine. In addition, natural organic nutrients such as starch hydrolysates, molasses, blackstrap molasses, rice bran, cassava, sugar cane bagasse, and corn steep liquor may be used, and specifically carbohydrates such as glucose and sterile pretreated molasses (i.e., molasses converted to reduced sugars) may be used, and suitable amounts of any other carbon sources may also be used without limitation. These carbon sources may be used alone or in combination of at least two thereof, but are not limited thereto.

The nitrogen sources may include inorganic nitrogen sources such as ammonia, ammonium sulfate, ammonium chloride, ammonium acetate, ammonium phosphate, ammonium carbonate, and ammonium nitrate; and organic nitrogen sources such as amino acids, e.g., glutamic acid, methionine, and glutamine, peptone, NZ-amine, meat extract, yeast extract, malt extract, corn steep liquor, casein hydrolysate, fish or degradation products thereof, and defatted soybean cake or degradation products thereof. These nitrogen sources may be used alone or in combination of at least two thereof, without being limited thereto.

The phosphorus sources may include monopotassium phosphate, dipotassium phosphate, or sodium-containing salts corresponding thereto. As inorganic compounds, sodium chloride, calcium chloride, iron chloride, magnesium sulfate, iron sulfate, manganese sulfate, calcium carbonate, and the like may be used. Also, amino acids, vitamins, and/or appropriate precursors may further be included. These components and precursors may be added to the culture medium in a batch or continuous process, without being limited thereto.

Also, during the culturing process of the microorganism, compounds such as ammonium hydroxide, potassium hydroxide, ammonia, phosphoric acid, and sulfuric acid may be added to the culture medium in a proper method to adjust the pH of the culture medium. Also, a defoaming agent such as fatty acid polyglycol ester may be added during culturing in order to inhibit formation of foams. In addition, oxygen or oxygen-containing gas may be injected into the culture medium to maintain the culture medium in an aerobic condition, or nitrogen, hydrogen, or carbon dioxide gas may be injected into the culture medium to maintain the culture medium in anaerobic and micro-aerobic conditions without injecting any other gases therefor, but the embodiment is not limited thereto.

The temperature of the culture medium may be maintained at 25° C. to 40° C., more specifically at 30° C. to 37° C., without being limited thereto. The culturing may be continued until a desired amount of a product is obtained, for example, for 0.5 hours to 60 hours, without being limited thereto.

The term "sulfur source" of the present disclosure may be used interchangeably with "source supplying sulfur" and refers to a sulfur-containing substance available in production of a sulfur-containing amino acid.

In culturing the microorganism, the sulfur source may be an important factor in determining a metabolic pathway in the microorganism. However, factors involved in transport of various sulfur sources and factors involved in degradation thereof have not been accurately revealed. For example, although it has been known that wild-type *Corynebacterium glutamicum* use various sulfur sources, it is known that the SsuD protein is not involved in transport of sulfate or sulfite but involved only in transport of aliphatic sulfonate (D. J. Koch, C. Ruckert, D. A. Rey, A. Mix, A. Puhler, J. Kalinowski. 2005. Role of the ssu and seu Genes of *Corynebacterium glutamicum* ATCC 13032 in Utilization of Sulfonates and Sulfonate Esters as Sulfur Sources. *AEM.* 71.10.6104-6114. 2005). That is, a protein transporting the sulfur source into a cell has substrate specificity. In addition, after the sulfur source is transported into the cell, an enzyme degrading the sulfur source may vary and a metabolic pathway using the same may also vary according to a structure and a functional group of the sulfur source. For example, when a sulfate is used as the sulfur source, it is known that CysZ transports the sulfate and CysDN, CysH, and CysI are involved until a sulfide is produced (Bolten, Christoph J., Hartwig Schroder, Jeroen Dickschat, and Christoph Wittmann. Towards Methionine Overproduction in *Corynebacterium glutamicum* Methanethiol and Dimethyldisulfide as Reduced Sulfur Sources. *J. Microbiol. Biotechnol.* (2010), 20(8), 1196-1203). However, in the case where thiosulfate is used as a sulfur source in production of sulfur-containing amino acids, factors used to transport and degrade thiosulfate have not been clearly revealed yet.

The sulfur source may be thiosulfate. Specifically, in the present disclosure, the sulfur source may include thiosulfate, such as ammonium thiosulfate or sodium thiosulfate or a mixture of thiosulfate and an organic or inorganic sulfur-containing compound such as sulfite, reduced raw material such as $H_2S$, sulfide, a derivative of sulfide, methylmercaptan, thioglycolite, thiocyanate, and thiourea. Alternatively, the sulfur source may not include any material other than thiosulfate. However, the embodiment is not limited thereto.

The method of producing the sulfur-containing amino acids or derivatives of the sulfur-containing amino acids may include recovering sulfur-containing amino acids or derivatives of the sulfur-containing amino acids from the microorganism or the culture medium.

The recovering step may be performed by collecting desired sulfur-containing amino acids or derivatives of the sulfur-containing amino acids using an appropriate method known in the art according to the culturing method of the present disclosure such as a batch, continuous, or fed-batch method. For example, centrifugation, filtration, treatment with a protein precipitating agent (salting out), extraction, ultrasonic disintegration, ultrafiltration, dialysis, various chromatographic methods such as molecular sieve chromatography (gel permeation), adsorption chromatography, ion-exchange chromatography, and affinity chromatography, high-performance liquid chromatography (HPLC), any combination thereof may be used, without being limited thereto.

The recovering step may further include a purifying process. The purifying process may be performed using an appropriate method known in the art.

Another aspect of the present disclosure provides a composition for producing a sulfur-containing amino acid or a derivative of the sulfur-containing amino acid, wherein the composition includes: a microorganism having enhanced activity of a protein encoded by ssuD gene compared to intrinsic activity or a culture thereof; and thiosulfate.

The protein encoded by ssuD gene, microorganism, thiosulfate and sulfur-containing amino acid are as described above.

The culture may be prepared by culturing the microorganism of the present disclosure in a culture medium.

The composition for producing a sulfur-containing amino acid or a derivative of the sulfur-containing amino acid according to the present disclosure may further include any component capable of assisting production of a sulfur-containing amino acid or a derivative of the sulfur-containing amino acid, and the component may be appropriately selected from those known in the art.

Another aspect of the present disclosure provides a use of a protein encoded by ssuD gene as a thiosulfate reductase.

Another aspect of the present disclosure provides a use of a microorganism including genetic modification to increase activity of a protein encoded by ssuD gene compared to a non-modified microorganism for producing sulfur-containing amino acids or derivatives of the sulfur-containing amino acids.

The protein encoded by ssuD gene, microorganism, cultures, thiosulfate, and sulfur-containing amino acid are as described above.

MODE FOR INVENTION

Hereinafter, the present disclosure will be described in more detail with reference to the following examples and experimental examples. However, the following examples and experimental examples are merely presented to exemplify the present disclosure, and the scope of the present disclosure is not limited thereto.

Example 1: Preparation of Recombinant Vector for Deletion of mcbR Gene

First, in order to prepare a strain producing methionine, as a representative sulfur-containing amino acid, *Corynebacterium glutamicum* ATCC 13032 strain was used to prepare a vector for inactivating known mcbR gene encoding a transcriptional regulator protein of methionine and cysteine (*J. Biotechnol.* 103:51-65, 2003).

Specifically, in order to delete the mcbR gene from the chromosome of the *Corynebacterium glutamicum* ATCC 13032 strain, a recombinant plasmid vector was prepared according to the following method.

Based on nucleotide sequences deposited in the U.S. National Institutes of Health (NIH) GenBank, the mcbR gene and flanking sequences (SEQ ID NO: 1) of *Corynebacterium glutamicum* were obtained.

PCR was performed using the chromosomal DNA of *Corynebacterium glutamicum* ATCC 13032 as a template and primers of SEQ ID NOS: 2, 3, 4, and 5. PCR was performed under the following conditions: denaturation at 95° C. for 5 minutes; 30 cycles of denaturation at 95° C. for 30 seconds, annealing at 53° C. for 30 seconds, and polymerization at 72° C. for 30 seconds; and polymerization at 72° C. for 7 minutes. As a result, DNA fragments of 700 bp were obtained, respectively.

A pDZ vector (U.S. Pat. No. 9,109,242 B2) unable to replicate in *Corynebacterium glutamicum* and the amplified mcbR gene fragments were treated with restriction enzyme SmaI for chromosomal insertion, followed by isothermal assembly cloning. *Escherichia coli* DH5α was transformed with the vector and plated on an LB solid medium containing 25 mg/L kanamycin. Colonies transformed with the vector into which a fragment having deletion of the target gene was inserted by PCR were selected, and then a plasmid was obtained by a plasmid extraction method and named pDZ-ΔmcbR.

Example 2: Preparation and Culture of mcbR Gene-Deleted Strain

The ATCC 13032 strain was transformed with the pDZ-ΔmcbR vector prepared in Example 1 above by electroporation by homologous chromosomal recombination (Van der Rest et al., *Appl Microbiol Biotechnol* 52:541-545, 1999). Subsequently, second recombination was performed in a solid medium containing sucrose. Upon completion of the second recombination, the transformed *Corynebacterium glutamicum* strain having deletion of mcbR gene was identified by performing PCR using SEQ ID NOS: 6 and 7, and the recombinant strain was named CM02-0618.

The CM02-0618 strain was deposited at the Korean Culture Center of Microorganisms under the Budapest Treaty on Jan. 4, 2019, with Accession No. KCCM12425P.

In order to analyze L-methionine producing ability of the prepared CM02-0618 strain, the strain and the parent strain, *Corynebacterium glutamicum* ATCC 13032 strain, were cultured in the following manner.

*Corynebacterium glutamicum* ATCC 13032 and *Corynebacterium glutamicum* CM02-0618 were inoculated onto a 250 mL corner-baffle flask containing 25 mL of a seed medium and cultured while shaking at 30° C. for 20 hours at 200 rpm. Then, 1 mL of a culture broth thereof was inoculated onto a 250 mL corner-baffle flask containing 24 mL of a production medium and cultured while shaking at 30° C. for 48 hours at 200 rpm. The compositions of the seed medium and the production medium are as follows. In the production medium, $(NH_4)_2S_2O_3$, which is one type of thiosulfate, was used as a sulfur source.

<Seed Medium (pH 7.0)>

20 g of glucose, 10 g of peptone, 5 g of yeast extract, 1.5 g of urea, 4 g of $KH_2PO_4$, 8 g of $K_2HPO_4$, 0.5 g of $MgSO_4 \cdot 7H_2O$, 100 μg of biotin, 1000 μg of thiamine HCl, 2000 μg of calcium pantothenate, and 2000 μg of nicotinamide (based on 1 L of distilled water).

<Production Medium (pH 8.0)>

50 g of glucose, 12 g of $(NH_4)_2S_2O_3$, 5 g of yeast extract, 1 g of $KH_2PO_4$, 1.2 g of $MgSO_4 \cdot 7H_2O$, 100 μg of biotin, 1000 μg of thiamine HCL, 2000 μg of calcium pantothenate, 3000 μg of nicotinamide, 30 g of $CaCO_3$, and 1 μg of cyanocobalamin (Vitamin B12) (based on 1 L of distilled water).

The strains were cultured according to the above-described culturing method and concentrations of L-methionine contained in the culture broth were analyzed and shown in Table 1 below.

TABLE 1

Confirmation of L-methionine producing ability of wild-type and mcbR gene-deleted strains

| Strain | L-Methionine (g/L) |
| --- | --- |
| *Corynebacterium glutamicum* ATCC 13032 (wild-type) | 0.00 |
| CM02-0618 | 0.04 |

As a result, it was confirmed that the L-methionine producing ability of the mcbR gene-deleted strain was enhanced by 0.04 g/L compared to that of the control strain. Also, it was confirmed that methionine was produced even when thiosulfate was used as a single sulfur source. Based thereon, it was assumed that a protein involved in utilizing thiosulfate may be present in a microorganism belonging to the genus *Corynebacterium*.

Example 3: Selection of Gene Involved in Utilizing Thiosulfate by Transcript Analysis No thiosulfate-specific protein of strains of the genus *Corynebacterium* is known. However, as confirmed in Example 2, the CM02-0618 strain produced methionine when thiosulfate was used as a single sulfur source, and thus an experiment was performed to select a protein involved in utilizing thiosulfate.

Specifically, after culturing the CM02-0618 strain prepared in Example 2 by changing only the sulfur source (ammonium sulfate and ammonium thiosulfate), Transcriptome analysis (analysis of RNA level) was performed. The same culturing method as that of Example 2 was used.

TABLE 2

Results of experiment on main gene transcripts of the CM02-0618 strain under the conditions using ammonium sulfate and ammonium thiosulfate

|  | AMS (signal) | ATS (signal) | Log2 ratio (ATS/AMS) |
|---|---|---|---|
| SsuD(Ncgl1173) | 3691 | 55539 | 2.71 |

Based on the results of the experiment, it was confirmed that an RNA level of a gene encoding SsuD (Ncgl1173) that is conventionally known as a sulfonate monooxygenase was significantly increased.

Thus, it was confirmed that the SsuD protein does not react with sulfate but specifically reacts with thiosulfate, and thus it may be assumed that the protein is involved in utilizing thiosulfate.

Example 4: Confirmation of Effects of ssuD Gene-Deleted Strain

In order to identify inactivation effects of SsuD protein selected as a protein specifically reacting with thiosulfate in Example 3, a vector was prepared to delete ssuD gene.

Example 4-1: Preparation of Vector for Deletion of ssuD Gene

In order to delete ssuD gene from the chromosome of *Corynebacterium* ATCC 13032 strain, a recombinant plasmid vector was prepared according to the following method.

Based on nucleotide sequences deposited in the U.S. National Institutes of Health (NIH) GenBank, the ssuD gene and flanking sequences (SEQ ID NO: 8) of *Corynebacterium glutamicum* were obtained.

For the purpose of deleting ssuD gene, PCR was performed using the chromosomal DNA of *Corynebacterium glutamicum* ATCC 13032 as a template and primers of SEQ ID NOS: 9, 10, 11, and 12. PCR was performed under the following conditions: denaturation at 95° C. for 5 minutes; 30 cycles of denaturation at 95° C. for 30 seconds, annealing at 53° C. for 30 seconds, and polymerization at 72° C. for 30 seconds; and polymerization at 72° C. for 7 minutes. As a result, DNA fragments of 700 bp were obtained, respectively.

A pDZ vector unable to replicate in *Corynebacterium glutamicum* and the amplified ssuD gene fragments were treated with the restriction enzyme SmaI for chromosomal insertion, followed by isothermal assembly cloning. *Escherichia coli* DH5α was transformed with the vector and plated on an LB solid medium containing 25 mg/L kanamycin. Colonies transformed with the vector into which a fragment having deletion of the target gene was inserted by PCR were selected, and then a plasmid was obtained by a plasmid extraction method and named pDZ-ΔSsuD.

Example 4-2: Preparation and Culture of ssuD Gene-Deleted Strain

13032/ΔmcbR strain was transformed with the pDZ-ΔSsuD vector prepared in Example 4-1 above by electroporation by homologous chromosomal recombination (Van der Rest et al., *Appl Microbiol Biotechnol* 52:541-545, 1999). Subsequently, second recombination was performed in a solid medium containing sucrose. Upon completion of the second recombination, the transformed *Corynebacterium glutamicum* strain having deletion of mcbR gene was identified by performing PCR using SEQ ID NOS: 13 and 14, and the recombinant strain was named *Corynebacterium glutamicum* CM02-0618/ΔSsuD.

Example 4-3: Analysis of Methionine Producing Ability of ssuD Gene-Deleted Strain In order to analyze L-methionine producing ability of the prepared CM02-0618/ΔSsuD strain, the strain and the parent strain, *Corynebacterium glutamicum* ATCC 13032 strain, were cultured in the following manner.

*Corynebacterium glutamicum* ATCC 13032, *Corynebacterium glutamicum* CM02-0618 prepared in Example 2, and CM02-0618/ΔSsuD were inoculated onto a 250 mL corner-baffle flask containing 25 mL of a seed medium and cultured while shaking at 30° C. for 20 hours at 200 rpm. Then, 1 mL of a culture broth thereof was inoculated onto a 250 mL corner-baffle flask containing 24 mL of a production medium and cultured while shaking at 30° C. for 48 hours at 200 rpm. The compositions of the seed medium and the production medium are as follows.

<Seed Medium (pH 7.0)>

20 g of glucose, 10 g of peptone, 5 g of yeast extract, 1.5 g of urea, 4 g of $KH_2PO_4$, 8 g of $K_2HPO_4$, 0.5 g of $MgSO_4 \cdot 7H_2O$, 100 μg of biotin, 1000 μg of thiamine HCl, 2000 μg of calcium pantothenate, and 2000 μg of nicotinamide (based on 1 L of distilled water).

<Production Medium (pH 8.0)>

50 g of glucose, 12 g of $(NH_4)_2S_2O_3$, 5 g of yeast extract, 1 g of $KH_2PO_4$, 1.2 g of $MgSO_4 \cdot 7H_2O$, 100 μg of biotin, 1000 μg of thiamine HCL, 2000 μg of calcium pantothenate, 3000 μg of nicotinamide, and 30 g of $CaCO_3$ (based on 1 L of distilled water).

The strains were cultured according to the above-described culturing method and concentrations of L-methionine contained in the culture broth were analyzed and shown in Table 3 below.

TABLE 3

Confirmation of L-methionine producing ability of ssuD gene-deleted strain

| Strain | L-Methionine (g/L) |
|---|---|
| CM02-0618 | 0.04 |
| CM02-0618/ΔSsuD | 0.02 |

As a result, it was confirmed that the L-methionine producing ability of the ssuD gene-deleted strain was reduced by about 50% compared to that of the control strain. Based thereon, it was confirmed that SsuD protein is a protein involved in utilizing thiosulfate.

Example 5: Preparation and Culture of ssuD Gene Expression-Increased Strain

A vector was prepared to enhance activity of SsuD protein selected as a protein specifically reacting with thiosulfate in Example 3.

Example 5-1: Preparation of Vector for Increasing Expression of ssuD Gene

In order to additionally inserting ssuD gene into the chromosome of *Corynebacterium* ATCC 13032, a plasmid vector was prepared according to the following method.

First, a vector for deleting Ncgl1464 (Transposase) was prepared to insert ssuD gene.

Based on nucleotide sequences deposited in the U.S. National Institutes of Health (NIH) GenBank, Ncgl1464 gene and flanking sequences (SEQ ID NO: 15) of *Corynebacterium glutamicum* were obtained. To delete Ncgl1464 gene, PCR was performed using the chromosomal DNA of *Corynebacterium glutamicum* ATCC 13032 as a template and primers of SEQ ID NOS: 16, 17, 18, and 19. PCR was performed under the following conditions: denaturation at 95° C. for 5 minutes; 30 cycles of denaturation at 95° C. for 30 seconds, annealing at 53° C. for 30 seconds, and polymerization at 72° C. for 30 seconds; and polymerization at 72° C. for 7 minutes. As a result, DNA fragments were obtained, respectively.

A pDZ vector unable to replicate in *Corynebacterium glutamicum* and the amplified Ncgl1464 gene fragments were treated with the restriction enzyme SmaI for chromosomal insertion, followed by isothermal assembly cloning. *Escherichia coli* DH5α was transformed with the vector and plated on an LB solid medium containing 25 mg/L kanamycin. Colonies transformed with the vector into which a fragment having deletion of the target gene was inserted by PCR were selected, and then a plasmid was obtained by a plasmid extraction method and named pDZ-ΔNcgl1464.

Subsequently, for the purpose of obtain ssuD gene fragments, PCR was performed using the chromosomal DNA of *Corynebacterium glutamicum* ATCC 13032 as a template and SEQ ID NOS: 20 and 21. In addition, a PgapA promoter was used to enhance expression of the ssuD gene. To obtain them, PCR was performed using the chromosomal DNA of the *Corynebacterium glutamicum* ATCC 13032 as a template using primers of SEQ ID NOS: 22 and 23. PCR was performed under the following conditions: denaturation at 95° C. for 5 minutes; 30 cycles of denaturation at 95° C. for 30 seconds, annealing at 53° C. for 30 seconds, and polymerization at 72° C. for 30 seconds; and polymerization at 72° C. for 7 minutes. As a result, ssuD gene fragments and gapA promoter fragments were obtained.

A pDZ-ΔNcgl1464 vector unable to replicate in *Corynebacterium glutamicum* was treated with the restriction enzyme ScaI, followed by IST reaction together with the two amplified DNA fragments. *Escherichia coli* DH5α was transformed with the vector and plated on an LB solid medium containing 25 mg/L kanamycin. Colonies transformed with the vector into which the target gene was inserted by PCR were selected, and then a plasmid was obtained by a plasmid extraction method and named pDZ-ΔNcgl1464-PgapASsuD.

Example 5-2: Preparation and Culture of ssuD Gene Expression-Enhanced Strain

CM02-0618 strain was transformed with the pDZ-ΔNcgl1464 and pDZ-ΔNcgl1464-PgapASsuD vectors prepared in Example 5-1 above by electroporation by homologous recombination (Van der Rest et al., *Appl Microbiol Biotechnol* 52:541-545, 1999). Subsequently, second recombination was performed in a solid medium containing sucrose. Upon completion of the second recombination, the transformed *Corynebacterium glutamicum* strain having deletion of Ncgl1464 gene and the *Corynebacterium glutamicum* strain having both deletion of Ncgl1464 gene and insertion of ssuD gene were identified by performing PCR using primers of SEQ ID NOS: 24 and 25. The strain having deletion of Ncgl1464 gene was named CM02-0618/ΔNcgl1464, and the stain having both deletion of Ncgl1464 gene and insertion of ssuD gene was named CM02-0736.

The CM02-0736 strain was deposited at the Korean Culture Center of Microorganisms under the Budapest Treaty on May 2, 2019, with Accession No. KCCM12512P.

Example 5-3: Analysis of Methionine Producing Ability of ssuD Gene Expression-Enhanced Strain In order to analyze L-methionine producing ability of the prepared CM02-0618/ΔNcgl1464 and CM02-0736 strains, the strains and the parent strain, CM02-0618 strain, were cultured in the following manner.

Each of the CM02-0618, CM02-0618/ΔNcgl1464, and CM02-0736 strains was inoculated onto a 250 mL corner-baffle flask containing 25 mL of a seed medium and cultured while shaking at 30° C. for 20 hours at 200 rpm. Then, 1 mL of a culture broth thereof was inoculated onto a 250 mL corner-baffle flask containing 24 mL of a production medium and cultured while shaking at 30° C. for 48 hours at 200 rpm. The compositions of the seed medium and the production medium are as follows.

<Seed Medium (pH 7.0)>

20 g of glucose, 10 g of peptone, 5 g of yeast extract, 1.5 g of urea, 4 g of $KH_2PO_4$, 8 g of $K_2HPO_4$, 0.5 g of $MgSO_4 \cdot 7H_2O$, 100 μg of biotin, 1000 μg of thiamine HCl, 2000 μg of calcium pantothenate, and 2000 μg of nicotinamide (based on 1 L of distilled water).

<Production Medium (pH 8.0)>

50 g of glucose, 12 g of $(NH_4)_2S_2O_3$, 5 g of yeast extract, 1 g of $KH_2PO_4$, 1.2 g of $MgSO_4 \cdot 7H_2O$, 100 μg of biotin, 1000 μg of thiamine HCL, 2000 μg of calcium pantothenate, 3000 μg of nicotinamide, 30 g of $CaCO_3$, and 1 μg of cyanocobalamin (Vitamin B12) (based on 1 L of distilled water).

The strains were cultured according to the above-described culturing method and concentrations of L-methionine contained in the culture broth were analyzed and shown in Table 4 below.

TABLE 4

| Confirmation of L-methionine producing ability of ssuD gene-enhanced strain | |
|---|---|
| Strain | L-Methionine (g/L) |
| CM02-0618 | 0.04 |
| CM02-0618/ΔNcgl1464 | 0.04 |
| CM02-0736 | 0.06 |

As a result, it was confirmed that the L-methionine producing ability of the ssuD gene expression-enhanced strain was increased by about 50% by enhancing expression of ssuD gene compared to that of the control strain. Also, it was confirmed that SsuD protein is involved in utilizing thiosulfate as confirmed in Example 4.

Example 6: Comparative Culture between Thiosulfate and Other Sulfonate

SsuD protein is known as a protein involved in desulfonation of sulfonate. Sulfonate, having a structure of R—$SO_3$, wherein R is an organic group, and is different from thiosulfate, which has a structure of S—$SO_3$.

Thus, effects of thiosulfate on methionine production was identified via a comparative experiment using sulfonate.

*Corynebacterium glutamicum* CM02-0618 and CM02-0736 strains were inoculated onto a 250 mL corner-baffle flask containing 25 mL of a seed medium and cultured while shaking at 30° C. for 20 hours at 200 rpm. Then, 1 mL of a culture broth thereof was inoculated onto a 250 mL corner-baffle flask containing 24 mL of a production medium and cultured while shaking at 30° C. for 48 hours at 200 rpm. The compositions of the seed medium and the production medium are as follows.

<Seed Medium (pH 7.0)>

20 g of glucose, 10 g of peptone, 5 g of yeast extract, 1.5 g of urea, 4 g of $KH_2PO_4$, 8 g of $K_2HPO_4$, 0.5 g of $MgSO_4 \cdot 7H_2O$, 100 µg of biotin, 1000 µg of thiamine HCl, 2000 µg of calcium pantothenate, and 2000 µg of nicotinamide (based on 1 L of distilled water).

<Production Medium (pH 8.0)>

50 g of glucose, 12 g of $(NH_4)_2S_2O_3$, methane sulfonate, or ethane sulfonate (depending on the sulfur source), 5 g of yeast extract, 1 g of $KH_2PO_4$, 1.2 g of $MgSO_4 \cdot 7H_2O$, 100 µg of biotin, 1000 µg of thiamine HCL, 2000 µg of calcium pantothenate, 3000 µg of nicotinamide, 30 g of $CaCO_3$, and 1 µg of cyanocobalamin (Vitamin B12) (based on 1 L of distilled water).

The strains were cultured according to the above-described culturing method and concentrations of L-methionine contained in the culture broth were analyzed and shown in Table 5 below.

TABLE 5

Comparison of methionine producing ability between thiosulfate and various sulfonates as sulfur sources

| Strain | Sulfur source | L-Methionine (g/L) |
|---|---|---|
| CM02-0618 | thiosulfate | 0.04 |
| | methane sulfonate | 0.01 |
| | ethane sulfonate | 0.01 |
| CM02-0736 | thiosulfate | 0.06 |
| | methane sulfonate | 0.01 |
| | ethane sulfonate | 0.02 |

As a result, in the case where thiosulfate was used as the sulfur source in each strain, the production of methionine increased by up to 600% compared to the case of using sulfonate as the sulfur source.

Based thereon, it was confirmed the production of methionine was the highest when thiosulfate was used as the sulfur source, and it was also confirmed that enhancement of the activity of SsuD protein is involved in such an increase in production of methionine.

Example 7: Preparation of Methionine-Producing Strain Having Enhanced Expression of metH and CysI Genes without Deleting mcbR Gene Example 7-1: Preparation of Recombinant Vector for Enhancing Both metH and CysI Genes In order to identify whether various a sulfur-containing amino acids may be produced by enhancing the activity of the SsuD protein of the present disclosure and using thiosulfate as a sulfur source, the above-described experiment was applied to another methionine-producing strain. First, in order to prepare a methionine-producing strain without deleting mcbR, a vector for enhancing both metH gene (Ncgl1450) encoding a methionine synthase and cysI gene (Ncgl2718) encoding a sulfite reductase in the ATCC 13032 strain was prepared.

Specifically, a recombinant plasmid vector was prepared to additionally insert metH and cysI genes into the chromosome of *Corynebacterium glutamicum* ATCC 13032 according to the following method. Based on nucleotide sequences deposited in the U.S. National Institutes of Health (NIH) GenBank, the metHgene and flanking sequences (SEQ ID NO: 26) and the cysI gene and flanking sequences (SEQ ID NO: 27) of *Corynebacterium glutamicum* were obtained.

First, a vector for deleting Ncgl1201 (Transposase) was prepared to insert these genes. Based on nucleotide sequences deposited in the U.S. National Institutes of Health (NIH) GenBank, Ncgl1021 gene and flanking sequences (SEQ ID NO: 28) of *Corynebacterium glutamicum* were obtained. To delete Ncgl1021 gene, PCR was performed using the chromosomal DNA of *Corynebacterium glutamicum* ATCC 13032 as a template and primers of SEQ ID NOS: 29, 30, 31, and 32. PCR was performed under the following conditions: denaturation at 95° C. for 5 minutes; 30 cycles of denaturation at 95° C. for 30 seconds, annealing at 53° C. for 30 seconds, and polymerization at 72° C. for 30 seconds; and polymerization at 72° C. for 7 minutes. As a result, DNA fragments were obtained. A pDZ vector unable to replicate in *Corynebacterium glutamicum* and the amplified Ncgl1021 gene fragments were treated with restriction enzyme XbaI for chromosomal insertion, followed by isothermal assembly cloning. *Escherichia coli* DH5α was transformed with the vector and plated on an LB solid medium containing 25 mg/L kanamycin. Colonies transformed with the vector into which a fragment having deletion of the target gene was inserted by PCR were selected, and then a plasmid was obtained by a plasmid extraction method and named pDZ-ΔNcgl1021.

Subsequently, for the purpose of obtaining metH and cysI genes, PCR was performed using the chromosomal DNA of *Corynebacterium glutamicum* ATCC 13032 as a template and primers of SEQ ID NOS: 33, 34, 35, and 36. In addition, a Pcj7 promoter was used to enhance expression of the metH gene and a Pspl1 promoter was used to enhance expression of the cyst gene. To obtain them, PCR was performed using the chromosomal DNA of the *Corynebacterium ammoniagenes* ATCC 6872 as a template and using primers of SEQ ID NOS: 37 and 38 for the Pcj7 promotor and PCR was performed using DNA of known spl1-GFP vector (U.S. Ser. No. 10/584,338 B2) as a template and using primers of SEQ ID NOS: 39 and 40 for the Pspl1 promotor. PCR was performed under the following conditions: denaturation at 95° C. for 5 minutes; 30 cycles of denaturation at 95° C. for 30 seconds, annealing at 53° C. for 30 seconds, and polymerization at 72° C. for 30 seconds; and polymerization at 72° C. for 7 minutes. As a result, DNA fragments of metH and cysI genes, Pcj7 promoter (U.S. Pat. No. 7,662,943 B2), and Pspl1 promoter (U.S. Ser. No. 10/584,338 B2) were obtained.

A pDZ-ΔNcgl1021 vector unable to replicate in *Corynebacterium glutamicum* was treated with the restriction enzyme ScaI and the amplified four DNA fragments were treated with the restriction enzyme ScaI, followed by IST reaction. *Escherichia coli* DH5α was transformed with the vector and plated on an LB solid medium containing 25 mg/L kanamycin. Colonies transformed with the vector into which the target gene was inserted by PCR were selected, and then a plasmid was obtained by a plasmid extraction method and named pDZ-ΔNcgl1021-Pcj7metH-Pspl1cysI.

Example 7-2: Development of L-Methionine-Producing Strain and Identification of L-Methionine Production Using the Same The ATCC 13032 strain was transformed with the pDZ-ΔNcgl1021 and pDZ-ΔNcgl1021-Pcj7metH-Pspl1 cyst vectors prepared in Example 7-1 above by electroporation by homologous chromosomal recombination (Van der Rest et al., *Appl Microbiol Biotechnol* 52:541-545, 1999). Subsequently, second recombination was performed in a solid medium containing sucrose. Upon completion of the second recombination, insertion of the Pcj7-metH-Pspl1 cyst gene into the transformed *Corynebacterium glutamicum* strain was identified using SEQ ID NOS: and 41 and 42. The recombinant strains were named *Corynebacterium glutamicum* 13032/ΔNcgl1021 (strain transformed with pDZ-ΔNcgl1021) and CM02-0753 (transformed with pDZ-ΔNcgl1021-Pcj7metH-Pspl1cysIn).

To analyze L-methionine producing ability of the prepared 13032/ΔNcgl1021 and CM02-0753 strains, the strains and the parent strain, *Corynebacterium glutamicum* ATCC 13032 strain, were cultured in the following manner.

*Corynebacterium glutamicum* ATCC 13032 and strains of the present disclosure, i.e., *Corynebacterium glutamicum* 13032/ΔNcgl1021 and CM02-0753 were inoculated onto a 250 mL corner-baffle flask containing 25 mL of a seed medium and cultured while shaking at 30° C. for 20 hours at 200 rpm. Then, 1 mL of a culture broth thereof was inoculated onto a 250 mL corner-baffle flask containing 24 mL of a production medium and cultured while shaking at 30° C. for 48 hours at 200 rpm. The compositions of the seed medium and the production medium are as follows.

<Seed Medium (pH 7.0)>

20 g of glucose, 10 g of peptone, 5 g of yeast extract, 1.5 g of urea, 4 g of $KH_2PO_4$, 8 g of $K_2HPO_4$, 0.5 g of $MgSO_4 \cdot 7H_2O$, 100 μg of biotin, 1000 μg of thiamine HCl, 2000 μg of calcium pantothenate, and 2000 μg of nicotinamide (based on 1 L of distilled water).

<Production Medium (pH 8.0)>

50 g of glucose, 12 g of $(NH_4)_2S_2O_3$, 5 g of yeast extract, 1 g of $KH_2PO_4$, 1.2 g of $MgSO_4 \cdot 7H_2O$, 100 μg of biotin, 1000 μg of thiamine HCL, 2000 μg of calcium pantothenate, 3000 μg of nicotinamide, 30 g of $CaCO_3$, and 1 μg of cyanocobalamin (Vitamin B12) (based on 1 L of distilled water).

The strains were cultured according to the above-described culturing method and concentrations of L-methionine contained in the culture broth were analyzed and shown in Table 6 below.

TABLE 6

Confirmation of L-methionine producing ability of mcbR gene-containing strain

| Strain | L-Methionine (g/L) |
|---|---|
| *Corynebacterium glutamicum* ATCC 13032 (wild-type) | 0 |
| 13032/ΔNcgl1021 | 0 |
| CM02-0753 | 0.03 |

As a result, it was confirmed that the L-methionine producing ability of the strain in which the mcbR gene was present and the metH and cysI genes were overexpressed was enhanced compared to that of the controls train. Based thereon, it was confirmed that the strain in which the metH and cysI genes were overexpressed without deleting the mcbR gene had the methionine producing ability, and the strain was used in the following experiment.

Example 8: Development of L-Methionine-Producing Strain Having Enhanced SsuD Activity and Including mcbR and Identification of L-Methionine Producing Ability A strain having enhanced activity of SsuD protein was prepared using the methionine-producing strain prepared in Example 7, and then the L-methionine producing ability thereof was identified.

Example 8-1: Preparation of Strain Having Enhanced SsuD Activity

Specifically, the CM02-0753 strain of Example 7 was transformed with the pDZ-ΔNcgl464-PgapASsuD vector prepared in Example 5 by electroporation by homologous chromosomal recombination (Van der Rest et al., *Appl Microbiol Biotechnol* 52:541-545, 1999). Subsequently, second recombination was performed in a solid medium containing sucrose.

Upon completion of the second recombination, insertion of PgapA-SsuD gene into the Ncgl1464 site of the transformed *Corynebacterium glutamicum* was identified using SEQ ID NOS: 23 and 24. The prepared recombinant strain was named *Corynebacterium glutamicum* CM02-0756.

The CM02-0756 was deposited at the Korean Culture Center of Microorganisms under the Budapest Treaty on May 2, 2019, with Accession No. KCCM12513P.

Example 8-2: Identification of Methionine Producing Ability of Prepared Strain

In order to analyze L-methionine producing ability of the prepared CM02-0753 strain of Example 7 and CM02-0756 strain prepared in Example 8-1, the strains were cultured in the following manner.

*Corynebacterium glutamicum* CM02-0753 and CM02-0756 strains were inoculated onto a 250 mL corner-baffle flask containing 25 mL of a seed medium and cultured while shaking at 30° C. for 20 hours at 200 rpm. Then, 1 mL of a culture broth thereof was inoculated onto a 250 mL corner-baffle flask containing 24 mL of a production medium and cultured while shaking at 30° C. for 48 hours at 200 rpm. The compositions of the seed medium and the production medium are as follows.

<Seed Medium (pH 7.0)>

20 g of glucose, 10 g of peptone, 5 g of yeast extract, 1.5 g of urea, 4 g of $KH_2PO_4$, 8 g of $K_2HPO_4$, 0.5 g of $MgSO_4 \cdot 7H_2O$, 100 μg of biotin, 1000 μg of thiamine HCl, 2000 μg of calcium pantothenate, and 2000 μg of nicotinamide (based on 1 L of distilled water).

<Production Medium (pH 8.0)>

50 g of glucose, 12 g of $(NH_4)_2S_2O_3$, 5 g of yeast extract, 1 g of $KH_2PO_4$, 1.2 g of $MgSO_4 \cdot 7H_2O$, 100 μg of biotin, 1000 μg of thiamine HCL, 2000 μg of calcium pantothenate, 3000 μg of nicotinamide, 30 g of $CaCO_3$, and 1 μg of cyanocobalamin (Vitamin B12) (based on 1 L of distilled water).

The strains were cultured according to the above-described culturing method and concentrations of L-methionine contained in the culture broth were analyzed and shown in Table 7 below.

TABLE 7

Confirmation of L-methionine producing ability of mcbR
gene-containing strain when ssuD gene is overexpressed

| Strain | L-Methionine (g/L) |
|---|---|
| CM02-0753 | 0.03 |
| CM02-0756 | 0.05 |

As a result, it was confirmed that the yield of L-methionine was increased in the methionine-producing strain including mcbR by enhancing activity of SsuD protein and using thiosulfate as the sulfur source.

These results indicate that sulfur-containing amino acids or derivatives of the sulfur-containing amino acids may be produced using thiosulfate as a sulfur source by enhancing the activity of SsuD protein that is newly confirmed in the present disclosure as a protein involved in utilizing thiosulfate.

The above description of the present disclosure is provided for the purpose of illustration, and it would be understood by those skilled in the art that various changes and modifications may be made without changing the technical conception and essential features of the present disclosure. Thus, it is clear that the above-described embodiments are illustrative in all aspects and do not limit the present disclosure. Therefore, the scope of the disclosure is defined not by the detailed description, but by the claims and their equivalents, and all variations within the scope of the claims and their equivalents are to be construed as being included in the disclosure.

What is claimed is:

1. A method of producing a sulfur-containing amino acid or a derivative of the sulfur-containing amino acid, the method comprising culturing a genetically modified microorganism in a culture medium including thiosulfate, and recovering the sulfur-containing amino acid or the derivative of the sulfur-containing amino acid from the microorganism or the culture medium,
   wherein the microorganism comprises a genetic modification to increase an expression level of a protein encoded by ssuD gene compared to a non-modified microorganism,
   wherein the production of the sulfur-containing amino acid by the microorganism comprising the genetic modification is increased compared to the non-modified microorganism;
   wherein the protein encoded by the ssuD gene comprises an amino acid sequence having at least 80% sequence identity to SEQ ID NO: 43.

2. The method of claim 1, wherein the protein encoded by ssuD gene has thiosulfate reductase activity.

3. The method of claim 1, wherein the protein encoded by ssuD gene comprises an amino acid sequence having at least 90% sequence identity to SEQ ID NO: 43.

4. The method of claim 1, wherein the microorganism is a microorganism belonging to the genus *Corynebacterium* or the genus *Escherichia* sp.

5. The method of claim 4, wherein the microorganism is *Corynebacterium glutamicum*, *Corynebacterium callunae*, *Corynebacterium deserti*, *Corynebacterium crenatum*, or *Escherichia coli*.

6. The method of claim 1, wherein genetic modification to increase the activity of the protein is achieved by i) increasing a copy number of a polynucleotide encoding the protein in a cell, ii) replacing an expression regulatory region of a polynucleotide encoding the protein with a sequence with stronger activity, iii) modifying an initiation codon or 5'-UTR of a polynucleotide encoding the protein, iv) modifying a nucleotide sequence on a chromosome to enhance the activity of the protein, v) introducing a foreign polynucleotide expressing the activity of the protein or a codon optimized variant polynucleotide of the polynucleotide encoding the protein, or vi) a combination thereof.

7. The method of claim 1, wherein the sulfur-containing amino acid or the derivative of the sulfur-containing amino acid comprises at least one selected from the group consisting of methionine, cysteine, cystine, lanthionine, homocysteine, homocystine, homolanthionine, and taurine.

* * * * *

SEQUENCE LISTING

<160> NUMBER OF SEQ ID NOS: 43

<210> SEQ ID NO 1
<211> LENGTH: 2642
<212> TYPE: DNA
<213> ORGANISM: Corynebacterium glutamicum

<400> SEQUENCE: 1

```
ctcccgcgca ctgctgcaat ccgcaccgtg cccaatgatg gtggttcgcc cacctgagaa      60
gattaagaag tagtttcttt taagtttcga tgccccggtt tcctgatttt gtgcagggag     120
gccggggcat tggtgtttgc gggttagttc gggccattcg aaagggagaa accaagggca     180
gccagacaga cgtgccaaga atctggattt ccgccaggtt ttggcacgcc cgtctggttt     240
aggcaatgag ataccgaaca cacgtgccaa aagttcggct ttttcgccga tcttgtcacg     300
cctgcctggt ttgtcttgta aagagtgatt tcatggccga gactcctaaa agtttgacct     360
cacaggattg cttctaaggg cctctccaat ctccactgag gtacttaatc cttccgggga     420
attcgggcgc ttaaatcgag aaattaggcc atcaccttt aataacaata caatgaataa      480
ttggaatagg tcgacaccct tggagcggag ccggttaaaa ttggcagcat tcaccgaaag     540
aaaaggagaa ccacatgctt gccctaggtt ggattacatg gatcattatt ggtggtctag     600
ctggttggat tgcctccaag attaaaggca ctgatgctca gcaaggaatt ttgctgaaca     660
tagtcgtcgg tattatcggt ggtttgttag gcggctggct gcttggaatc ttcggagtgg     720
atgttgccgg tggcggcttg atcttcagct tcatcacatg tctgattggt gctgtcattt     780
tgctgacgat cgtgcagttc ttcactcgga agaagtaatc tgctttaaat ccgtagggcc     840
tgttgatatt tcgatatcaa caggccttt ggtcattttg gggtggaaaa agcgctagac       900
ttgcctgtgg attaaaacta tacgaaccgg tttgtctata ttggtgttag acagttcgtc     960
gtatcttgaa acagaccaac ccgaaaggac gtggccgaac gtggctgcta gcgcttcagg    1020
caagagtaaa acaagtgccg gggcaaaccg tcgtcgcaat cgaccaagcc cccgacagcg    1080
tctcctcgat agcgcaacca accttttcac cacagaaggt attcgcgtca tcggtattga    1140
tcgtatcctc cgtgaagctg acgtggcgaa ggcgagcctc tattcccttt tcggatcgaa    1200
ggacgccttg gttattgcat acctggagaa cctcgatcag ctgtggcgtg aagcgtggcg    1260
tgagcgcacc gtcggtatga aggatccgga agataaaatc atcgcgttct ttgatcagtg    1320
cattgaggaa gaaccagaaa aagatttccg cggctcgcac tttcagaatg cggctagtga    1380
gtaccctcgc cccgaaactg atagcgaaaa gggcattgtt gcagcagtgt tagagcaccg    1440
```

```
cgagtggtgt cataagactc tgactgattt gctcactgag aagaacggct acccaggcac    1500
cacccaggcg aatcagctgt tggtgttcct tgatggtgga cttgctggat ctcgattggt    1560
ccacaacatc agtcctcttg agacggctcg cgatttggct cggcagttgt tgtcggctcc    1620
acctgcggac tactcaattt agtttcttca ttttccgaag gggtatcttc gttgggggag    1680
gcgtcgataa gccccttctt tttagcttta acctcagcgc gacgctgctt taagcgctgc    1740
atggcggcgc ggttcatttc acgttgcgtt tcgcgcctct tgttcgcgat ttctttgcgg    1800
gcctgttttg cttcgttgat ttcggcagta cgggttttgg tgagttccac gtttgttgcg    1860
tgaagcgttg aggcgttcca tggggtgaga atcatcaggg cgcggttttt gcgtcgtgtc    1920
cacaggaaga tgcgcttttc tttttgtttt gcgcggtaga tgtcgcgctg ctctaggtgg    1980
tgcactttga aatcgtcggt aagtgggtat ttgcgttcca aaatgaccat catgatgatt    2040
gtttggagga gcgtccacag gttgttgctg acccaataga gtgcgattgc tgtggggaat    2100
ggtcctgtga ggccaaggga cagtgggaag atcggcgcga ggatcgacat cacgatcatg    2160
aacttcagca tgccgttaga gaatccggat gcgtaatcgt tggtttggaa gctgcggtac    2220
atggacatcg ccatgttgat tgcggtgagg attgcggctg tgatgaacag tggcaaaacg    2280
aaactaagaa cttccgcctg cgtggtgctc aaatatttta gctgctcagt gggcatcgaa    2340
acataagcgg gcagaggcac attgctcacg cgaccagcga ggaaagattc cacttcctca    2400
ggagttagga agccgatcga ctggaagacg ggattttcca aaccaccttc agggcgagcc    2460
atgcggagaa gtgcccagta aagaccaagg acaatcggta tctggatcag cccaggcaca    2520
caacctgcca gcgggttaat gccgtattcc ttattcaaat cattctggcg cttctgcaac    2580
tcccgaatgg acgcttcatc gtactttccc ttgtattctt cccggagcgc agcgcggtga    2640
gg                                                                   2642

<210> SEQ ID NO 2
<211> LENGTH: 34
<212> TYPE: DNA
<213> ORGANISM: Artificial Sequence
<220> FEATURE:
<223> OTHER INFORMATION: primer

<400> SEQUENCE: 2
tcgagctcgg taccccctgcc tggtttgtct tgta                                34

<210> SEQ ID NO 3
<211> LENGTH: 35
<212> TYPE: DNA
<213> ORGANISM: Artificial Sequence
<220> FEATURE:
<223> OTHER INFORMATION: primer

<400> SEQUENCE: 3
cggaaaatga agaaagttcg gccacgtcct ttcgg                                35

<210> SEQ ID NO 4
<211> LENGTH: 35
<212> TYPE: DNA
<213> ORGANISM: Artificial Sequence
<220> FEATURE:
<223> OTHER INFORMATION: primer

<400> SEQUENCE: 4
aggacgtggc cgaactttct tcattttccg aaggg                                35
```

```
<210> SEQ ID NO 5
<211> LENGTH: 35
<212> TYPE: DNA
<213> ORGANISM: Artificial Sequence
<220> FEATURE:
<223> OTHER INFORMATION: primer

<400> SEQUENCE: 5
ctctagagga tccccgtttc gatgcccact gagca                              35

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
aatctggatt tccgccaggt                                               20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
cttcctaact cctgaggaag                                               20

<210> SEQ ID NO 8
<211> LENGTH: 3146
<212> TYPE: DNA
<213> ORGANISM: Corynebacterium glutamicum

<400> SEQUENCE: 8
ccatggagaa cctggagaat gaggtgctgc gtcgttccac gcaggttccg gtgattgttc     60
tcgtgggtac cccgcgcagc cctgattcgg agcagttgaa gtcggatctg accacgcttg    120
ctgctgaaag tggcaggaag ttcatttttcg gttatgtcaa tgctgatacc gatgctgatg    180
tggcccaggt gtttggggtg cagggcttgc cgtcggtgat tgctgtggca gcgggacgcc    240
ctctggctga tttccagggc ggacagccag cggatgcact aaagcagtgg actgatcagg    300
tggttcaggc tgtgggtgga cagctggaag gactgccaga ggaggccaca gacggcgaac    360
aagaagacgc tcctgtggaa gaccccgct tcgatgctgc cactgatgct ctaaaccgtg    420
gcgctttcga tgaggcgatt gcggtttatg agtccatttt ggcgcaggag ccaaacaacg    480
ctgatgcgaa gcaggcacgc gataccgcaa agctgttggg ccggcttgcc acggtggatc    540
cttcggtgga tgttgtcgct gctgcagatg ctgatccaac aaacgttgat ctggcctaca    600
cagcagctga cgcggctgtt gttgcgggtg atcctgaggc tgcctttgat cgtttaattg    660
ctctgctgac catcagcgct ggcgatcaga agaatcaggt gaaggaacgt ttgctggagc    720
tgtttggcat gtttgagacc gccgatcccc gtgtgctgca ggcgcgagga agatggcca    780 gcgcgctgtt ctaaaaccac tctctatcca gaaaaatata daccgcttag tcttttccag    840
gactaagtgg tctacatttt tacccaaaat gcagctcacg caatagacat ctcggtctat    900 atcttgcca ccttcgcgcc ctgcaaatcc ccacactact tatatccagc ccgaaaataa    960
tacttctctc tagacgaagc ggtctgttta agtatgtgcc atgacattaa ctttccattg   1020
gttcctatcc acttcaggcg attcccgcgg catcatcggc ggcggtcacg gtgcagaaaa   1080
```

```
atccggcacc tcccgcgaat tgagccacag ctacctcaag cagttggcgc tagctgccga    1140
gaccaacggt tttgaatctg tcctgacacc aacgggcacg tggtgcgaag atgcgtggat    1200
tactgacgct tctttgattg aggcgacaaa acgcttgaag ttcctcgttg cgcttcgccc    1260
tgggcagatt ggacctacgc tgtctgctca aatggcttct actttccagc gtctgtctgg    1320
caaccgtttg ctgatcaatg tggtcaccgg tggggaagat gcggagcagc gtgcgtttgg    1380
tgatttcttg aacaaggagg agcgctacgc ccgtaccgga gaattcttgg atatcgtgag    1440
ccgcttgtgg cgaggcgaaa ccgtcacgca ccacggtgaa cacctgcagg tggagcaagc    1500
tagccttgcg catccgccag agattattcc ggagattctt tttggtggat cgtcgccagc    1560
tgcaggtgag gtggctgcac gttatgcgga cacctatctc acgtggggtg aaactcccga    1620
tcaggtggcg cagaaaatca actggatcaa cgagctagca gcacagcgcg ccgggaact    1680 gcgccatgga atccgcttcc atgtgatcac ccgcgatacg tctgaagaag catgggtggt    1740
ggcagagaag ttgattagcg gggtcactcc agaacaggtc gctaaggctc aagccgggtt    1800
tgcaacgtct aagtcggagg ggcagcgccg gatggctgag ctgcacagca agggtcgtgc    1860
ctttactagt ggctcaactg ctcgtgatct ggaggtgtat cccaatgtgt gggcaggcgt    1920
cggtttgctt cgcggaggtg caggaacagc ccttgtgggc tcgcatgaag aggtcgccga    1980
tcgcatcgaa gaatacgcag cactcggctt ggatcagttt gtactgtcgg gttatccaaa    2040
cttggaggag gccttccact tcggtgaggg tgtgattccg gagctgctgc cccgcggtgt    2100
ggatatcaaa aatcaagaat cacgagtttt ggaacctgtt gggtaaacgg aagaacgag     2160 acgtcgataa gcaaatttct taaggaacct gacatgacta caaccttgac tcgccccaaa    2220
atcgcgctgc ccgcgcgcat ctattcaccg cttgcggtgc ttgttttctg gcagctcggc    2280
tcgagcctgg gcgccatccc ggagcggatt ctgccggcac caaccacgat cttggccgcc    2340
agctgggagg tcgccacaaa tggcacgctt ctcgacgccc tcctcgtctc aagccaacgc    2400
gtccttctag gcttcgccct cggtgctgtc ctaggcattt ccctaggtgt attgacaggc    2460
atgtccagat ttgcagacac cgccgttgat ccgctcattc aagctgcccg cgcgctgcct    2520
cacctgggtc ttgtgccgct gtttatcatc tggttcggta tcggtgagct gccgaaagta    2580
ctgattatta gcctcggcgt gctgtatccg ctgtacctca acaccgccag cgggttcagg    2640
caaattgatc aaagcttct ggaagccggc cacgtgatgg gcttcggatt tttccagagg    2700
ttgcggacca tcatcattcc ttctgccgcg ccgcaacttt tgtcggcct gcgccaagca    2760 agtgcggccg cctggctctc actgatcgtg cggaacagg tcaacgcccg cgaaggactc    2820
ggcttcctca tcaacaatgc gcgcgatttt taccgcaccg acctcgttat tttcggcctc    2880
attgtctacg ccagcctcgg tctgctgtct gaagcgctga tcagagcttg gaacgtcac    2940 accttccgct accgaaacgc ataagaaagt tgctcgccat gactgccaca ttgtcactca    3000
aacccgcagc cactgtccgt ggattgcgca aatcatacgg aactaaagaa gtcctccaag    3060
gaatcgacct caccatcaac tgcggcgaag taaccgcgct gatcggacgc tcaggttcag    3120
gaaaatccac catcctgcgc gtgttg                                          3146
```

<210> SEQ ID NO 9
<211> LENGTH: 35
<212> TYPE: DNA
<213> ORGANISM: Artificial Sequence
<220> FEATURE:
<223> OTHER INFORMATION: primer

<400> SEQUENCE: 9
tcgagctcgg taccctggtt caggctgtgg gtgga        35

<210> SEQ ID NO 10
<211> LENGTH: 35
<212> TYPE: DNA
<213> ORGANISM: Artificial Sequence
<220> FEATURE:
<223> OTHER INFORMATION: primer

<400> SEQUENCE: 10
tcttcccgta gtactggcac atacttaaac agacc        35

<210> SEQ ID NO 11
<211> LENGTH: 35
<212> TYPE: DNA
<213> ORGANISM: Artificial Sequence
<220> FEATURE:
<223> OTHER INFORMATION: primer

<400> SEQUENCE: 11
gtatgtgcca gtactacggg aagaacgaga cgtcg        35

<210> SEQ ID NO 12
<211> LENGTH: 35
<212> TYPE: DNA
<213> ORGANISM: Artificial Sequence
<220> FEATURE:
<223> OTHER INFORMATION: primer

<400> SEQUENCE: 12
ctctagagga tcccctcgcg cgcattgttg atgag        35

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
ccaggtgttt ggggtgcagg        20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
aatccacgga cagtggctgc        20

<210> SEQ ID NO 15
<211> LENGTH: 3161
<212> TYPE: DNA
<213> ORGANISM: Corynebacterium glutamicum

<400> SEQUENCE: 15
agacgattct ggaaggccac tttcttttga tcctggcggc gattttttcgg tgcttggtag        60 cggaatgtca atcgagacca agcgtccccc ggcgggtcga ttttttggtc tcgaatgaca       120
gtttcgctct ctggaaactc tcagtgtcag gtcagtggtg aaccaccatc cttagcaagg       180
agttcatcat gtccatcccc ttctcagtcc ttcaggacta cctggatctg atcagtcccg       240

-continued

```
aagccttacc ccagatccca cagccccgg ccctgcccc cacagcaccc cagctaccac      300
cggcgccgga cccacacagc atcgagtggc cgatcttccc accagatcga atctccgcca    360
acgggcgacg ctactacgag ccacaaacac gactcgagtt catgcggatc tacaccaccc    420
tgccgcacgg ctaccgccag cccttcctta aagccaacaa catcggccac tgcaccgttc    480
gaacctggct agcagcaata agcaccttca gccgacttcc ccatgctttt gatgatgccc    540
accgcttcgg gatcgaacgc accaccccag tcgacgatgt caccacacta acggctgatg    600
acaaacgtga cctggtcata ggatacttag ctcaaccaca cggtcagggc cagcaattcc    660
tcacgtttta ccaactccgt aagcacacca tcatggcctg gtcgccgct atgaccgacg     720
gggacttaga cgctgatatc tcaccccgcc agatcgggtt gatgaccacc cgaaccgtgg    780
tcgaaatcgt tcgactacgc cacatgattg cccaacaact agaaagagcc acgatcatgg    840
aaaacgagta cctcaaagaa atcgcagcgc tgaagaaaga actcgcgcac tacaagcaaa    900
aagaccatca gaatcaaatg gtgatcgata tcttgggaaa agctattggg accaggccca    960
atcctggcga gggcttagac gaggaggacg ccacctaaac gtggatgagc aacgcgcctt   1020
tgatcaagga ctcaaggaag aaaacaccct tgatcacagat ctcaccacct gtgccaggct  1080
gagccataac aaggcattac ggctgatcaa gctgtcgaaa tcaacggcgt attaccgcaa   1140
caagccgcgt ccccgtcctg caccgaaacc tgtcctgcag gccgtgccag caccaacagc   1200
acctggtgtg gaacccacac cagagccttg gcagggaag gagccagcag tgtcgtcggt    1260
gcgtcaagcg ttggcagaac acgaacgcca gttcattgtt gatgcgatca ccgcgtaccc   1320
acaactgagc gttagtgggg tgtttaacat gttgtttaac aaaggcatct accgcgcatc   1380
actacgtaca tggtggcgtg ttgccaagca gcacaagttg ttacacaaag accgagtcag   1440
tgccctgtcc ccggggaaac gatcaccaac gccacgggtt aagccgaggt tggaagcaac   1500
acagcctggt caggtggtgt gttgggatgt gacgttcttg ccgtcgctgg tacgtggtaa   1560
gacctatgcg ttgcatctgg cgattgattt gttttcccgc aagattgttg gggcgaaggt   1620
cgcgccgacg gaaaatacct ccaccgcggt ggagttgtta acgcaggtgt tagcggataa   1680
tccgggtgtg gtgacggtgc attcggataa tgggtcggcg atgacatcga cgagggtgcg   1740
gcggttgtta gcggatcatg gtgtggcgtt gtcgttgatt cggccgcggg tgagtgatga   1800
taatgcgttt gtggagtcgg tgtttcatac gttgaagtat cggccgtttt atccgaaggt   1860
gtttgcatcg atggatcagg cccgggtgtg ggtggaggag tttgtggtgt attacaacac   1920
ggttcatccg cattctggtg tggctgggca tactccgcag tcggtgtttg atggtagttg   1980
gagggcggct cataggttgc gtgtgcaggc gttggatgcc cattaccggc agttcccgca   2040
gcggtatgtg gggcggccgg tggttcagga agttgctggt gtggtgcgtc ttaatggtgc   2100
gcgtgatgat gggtctgtac aggagagggt tggtggtgta gcgtcgctgt taagtgcttg   2160
agttagcatg tgttcttatc gccccctgg ttcacaaacc cctggcagcg agcggaaaag    2220
tgcatttta ggccaagggc cctcggatct tcgagcgctt tggtctcttt tgcacgtctg   2280
accgaaccag atcacctaga aacgccaaag gccccgcaag tatcaaacct gcggggcctt   2340
tgaggtacct gtttcctatt tgttgactt aggaagctgc gcacggcgga taaccaaacc    2400
gcacagcaag gcagccactc cccacgcggt gagccagaac tgctccacga cataaacctg   2460
aatagttgga agcaaacgac ttacgatcac cagggctaca gcgatgctca aagaaatgat   2520
ctgtgtcttt gagcttggct cgtacttgct ggtggtagcg aatgcgccga gaatgatcga   2580
ggcaacgagg atcagaagga atcctggagt gatcacaaat gggctcagca tgccggcggt   2640
```

```
aaacagctca attgctgcaa acaccaacaa aaccagacct aaggctacga aagctccacc    2700
gatgcggatt gctgccggaa ctttacgcca gctggcacgg ccttcgaggc tggtgagctt    2760
ttttaatgat cttcccgatg ctgaactcat aatgtgacat accctactag ttctcgtacc    2820
atccccacac aattgacctg ccaagagtgt ggaaatacag gttgaagcct agaacagtgg    2880
gggtagcgtc gggggcgatg tcgagttttt ccacatcaag tgcatgaact gcgaagaggt    2940
aacggtgcgg tgcgtggcca gctggaggtt gcgctccgta gaagccacgc ttgccggaat    3000 caccettgag ggaaactacg ccttcgatgc cgccgagggt ttcatcgcca gcaccggtgg    3060
ggatctccgt gacagttgtg gggatgttaa acactgccca gtgccagaaa ccagcgccgg    3120
ttggggcatc tgggtcgagg caggtgatcg cgagggattt g                       3161
```

<210> SEQ ID NO 16
<211> LENGTH: 35
<212> TYPE: DNA
<213> ORGANISM: Artificial Sequence
<220> FEATURE:
<223> OTHER INFORMATION: primer

<400> SEQUENCE: 16

```
tcgagctcgg tacccttttt tggtctcgaa tgaca                                35
```

<210> SEQ ID NO 17
<211> LENGTH: 35
<212> TYPE: DNA
<213> ORGANISM: Artificial Sequence
<220> FEATURE:
<223> OTHER INFORMATION: primer

<400> SEQUENCE: 17

```
catgctaaca gtactgttta ggtggcgtcc tcctc                                35
```

<210> SEQ ID NO 18
<211> LENGTH: 35
<212> TYPE: DNA
<213> ORGANISM: Artificial Sequence
<220> FEATURE:
<223> OTHER INFORMATION: primer

<400> SEQUENCE: 18

```
gtatgtgcca gtactacggg aagaacgaga cgtcg                                35
```

<210> SEQ ID NO 19
<211> LENGTH: 35
<212> TYPE: DNA
<213> ORGANISM: Artificial Sequence
<220> FEATURE:
<223> OTHER INFORMATION: primer

<400> SEQUENCE: 19

```
ctctagagga tcccctcgcg cgcattgttg atgag                                35
```

<210> SEQ ID NO 20
<211> LENGTH: 35
<212> TYPE: DNA
<213> ORGANISM: Artificial Sequence
<220> FEATURE:
<223> OTHER INFORMATION: primer

<400> SEQUENCE: 20

```
tagaggagac acaacatgac attaactttc cattg                                35
```

```
<210> SEQ ID NO 21
<211> LENGTH: 35
<212> TYPE: DNA
<213> ORGANISM: Artificial Sequence
<220> FEATURE:
<223> OTHER INFORMATION: primer

<400> SEQUENCE: 21
acacatgcta acagtttacc caacaggttc caaaa                        35

<210> SEQ ID NO 22
<211> LENGTH: 35
<212> TYPE: DNA
<213> ORGANISM: Artificial Sequence
<220> FEATURE:
<223> OTHER INFORMATION: primer

<400> SEQUENCE: 22
cgccacctaa acagtgaagc ctaaaaacga ccgag                        35

<210> SEQ ID NO 23
<211> LENGTH: 35
<212> TYPE: DNA
<213> ORGANISM: Artificial Sequence
<220> FEATURE:
<223> OTHER INFORMATION: primer

<400> SEQUENCE: 23
gaaagttaat gtcatgttgt gtctcctcta aagat                        35

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
ctggcggcga ttttcggtg                                          20

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
cgcgatcacc tgcctcgacc                                         20

<210> SEQ ID NO 26
<211> LENGTH: 5666
<212> TYPE: DNA
<213> ORGANISM: Corynebacterium glutamicum

<400> SEQUENCE: 26
tgtcatgctt ccggaggtgc gcagggctcg agactccgga aagctatttg ccactccgat    60
gtttgggtca ctcgacgaga tacgtgctga tcacctaatt tggtgcacag ggtttcggcc   120
ggcgattagg ccagttcgtc aacttctcaa acacggacaa ccaaaggttc ctggtctta    180 tttagtaggc tacggagatt ggacgggacc tgggtctgcg actatacacag gggtcgggct   240 ttatgccaag cgagcagcca aagagattgc cgcgtcagtc ggcaaagtcg ttaaatagtt   300
tgaaggctaa gaacttaatg ttaaagcgaa aattgttttg acacctcaac taatgcagcg   360
```

```
atgcgttctt tccagaatgc tttcatgaca gggatgctgt cttgatcagg caggcgtctg     420
tgctggatgc cgaagctgga tttattgtcg cctttggagg tgaagttgac gctcactcga     480
gaatcatcgg ccaaccattt ggcattgaat gttctaggtt cggaggcgga ggttttctca     540
attagtgcgg gatcgagcca ctgcgcccgc aggtcatcgt ctccgaagag cttccacact     600
ttttcgaccg gcaggttaag ggttttggag gcattggccg cgaacccatc gctggtcatc     660
ccgggtttgc gcatgccacg ttcgtattca taaccaatcg cgatgccttg agcccaccag     720
ccactgacat caaagttgtc cacgatgtgc tttgcgatgt gggtgtgagt ccaagaggtg     780
gcttttacgt cgtcaagcaa ttttagccac tcttcccacg gctttccggt gccgttgagg     840
atagcttcag gggacatgcc tggtgttgag ccttgcggag tggagtcagt catgcgaccg     900
agactagtgg cgctttgcct gtgttgctta ggcggcgttg aaaatgaact acgaatgaaa     960
agttcgggaa ttgtctaatc cgtactaagc tgtctacaca atgtctactt cagttacttc    1020
accagcccac aacaacgcac attcctccga attttggat  gcgttggcaa accatgtgtt    1080
gatcggcgac ggcgccatgg gcacccagct ccaaggcttt gacctggacg tggaaaagga    1140
tttccttgat ctggagggt  gtaatgagat tctcaacgac acccgccctg atgtgttgag    1200
gcagattcac cgcgcctact ttgaggcggg agctgacttg gttgagacca atacttttgg    1260
ttgcaacctg ccgaacttgg cggattatga catcgctgat cgttgccgtg agcttgccta    1320
caagggcact gcagtggcta gggaagtggc tgatgagatg gggccgggcc gaaacggcat    1380
gcggcgtttc gtggttggtt ccctgggacc tggaacgaag cttccatcgc tgggccatgc    1440
accgtatgca gatttgcgtg gcactacaa  ggaagcagcg cttggcatca tcgacggtgg    1500
tggcgatgcc ttttgattg  agactgctca ggacttgctt caggtcaagg ctgcggttca    1560
cggcgttcaa gatgccatgg ctgaacttga tacattcttg cccattattt gccacgtcac    1620
cgtagagacc accggcacca tgctcatggg ttctgagatc ggtgccgcgt tgacagcgct    1680
gcagccactg ggtatcgaca tgattggtct gaactgcgcc accggcccag atgagatgag    1740
cgagcacctg cgttacctgt ccaagcacgc cgatattcct gtgtcggtga tgcctaacgc    1800
aggtcttcct gtcctgggta aaaacggtgc agaatacca  cttgaggctg aggatttggc    1860
gcaggcgctg gctggattcg tctccgaata tggcctgtcc atggtgggtg ttgttgtgg     1920 caccacacct gagcacatcc gtgcggtccg cgatgcggtg gttggtgttc cagagcagga    1980
aacctccaca ctgaccaaga tccctgcagg ccctgttgag caggcctccc gcgaggtgga    2040
gaaagaggac tccgtcgcgt cgctgtacac ctcggtgcca ttgtcccagg aaaccggcat    2100
ttccatgatc ggtgagcgca ccaactccaa cggttccaag gcattccgtg aggcaatgct    2160 gtcctggcgat tgggaaaagt gtgtggatat tgccaagcag caaacccgcg atggtgcaca    2220
catgctggat ctttgtgtgg attacgtggg acgagacggc accgccgata tggcgacctt    2280
ggcagcactt cttgctacca gctccacttt gccaatcatg attgactcca ccgagccaga    2340
ggttattcgc acaggccttg agcacttggg tggacgaagc atcgttaact ccgtcaactt    2400
tgaagacggc gatggccctg agtcccgcta ccagcgcatc atgaaactgg taaagcagca    2460
cggtgcggcc gtggttgcgc tgaccattga tgaggaaggc caggcacgta ccgctgagca    2520
caaggtgcgc attgctaaac gactgattga cgatatcacc ggcagctacg gcctggatat    2580
caaagacatc gttgtggact gcctgacctt cccgatctct actggccagg aagaaaccag    2640
gcgagatggc attgaaacca tcgaagccat ccgcgagctg aagaagctct acccagaaat    2700
```

```
ccacaccacc ctgggtctgt ccaatatttc cttcggcctg aaccctgctg cacgccaggt    2760
tcttaactct gtgttcctca atgagtgcat tgaggctggt ctggactctg cgattgcgca    2820
cagctccaag attttgccga tgaaccgcat tgatgatcgc cagcgcgaag tggcgttgga    2880
tatggtctat gatcgccgca ccgaggatta cgatccgctg caggaattca tgcagctgtt    2940
tgagggcgtt tctgctgccg atgccaagga tgctcgcgct gaacagctgg ccgctatgcc    3000
tttgtttgag cgtttggcac agcgcatcat cgacggcgat aagaatggcc ttgaggatga    3060
tctggaagca ggcatgaagg agaagtctcc tattgcgatc atcaacgagg accttctcaa    3120
cggcatgaag accgtgggtg agctgtttgg ttccggacag atgcagctgc cattcgtgct    3180
gcaatcggca gaaaccatga aaactgcggt ggcctatttg gaaccgttca tggaagagga    3240
agcagaagct accggatctg cgcaggcaga gggcaagggc aaaatcgtcg tggccaccgt    3300
caagggtgac gtgcacgata tcggcaagaa cttggtggac atcatttttgt ccaacaacgg    3360 ttacgacgtg gtgaacttgg gcatcaagca gccactgtcc gccatgttgg aagcagcgga    3420
agaacacaaa gcagacgtca tcggcatgtc gggacttctt gtgaagtcca ccgtggtgat    3480
gaaggaaaac cttgaggaga tgaacaacgc cggcgcatcc aattacccag tcattttggg    3540
tggcgctgcg ctgacgcgta cctacgtgga aaacgatctc aacgaggtgt acaccggtga    3600
ggtgtactac gcccgtgatg ctttcgaggg cctgcgcctg atggatgagg tgatggcaga    3660
aaagcgtggt gaaggacttg atcccaactc accagaagct attgagcagg cgaagaagaa    3720
ggcggaacgt aaggctcgta atgagcgttc ccgcaagatt gccgcggagc gtaaagctaa    3780
tgcggctccc gtgattgttc cggagcgttc tgatgtctcc accgatactc caaccgcggc    3840
accaccgttc tggggaaccc gcattgtcaa gggtctgccc ttggcggagt cttgggcaa     3900 ccttgatgag cgcgccttgt tcatgggca gtggggtctg aaatccaccc gcggcaacga    3960
gggtccaagc tatgaggatt tggtggaaac tgaaggccga ccacgcctgc gctactggct    4020
ggatcgcctg aagtctgagg gcattttgga ccacgtggcc ttggtgtatg gctacttccc    4080
agcggtcgcg gaaggcgatg acgtggtgat cttggaatcc ccggatccac acgcagccga    4140
acgcatgcgc tttagcttcc cacgccagca gcgcggcagg ttcttgtgca tgcggatt     4200 cattcgccca cgcgagcaag ctgtcaagga cggccaagtg gacgtcatgc cattccagct    4260
ggtcaccatg gtaatcccta ttgctgattt cgccaacgag ttgttcgcag ccaatgaata    4320
ccgcgagtac ttgaagttc acggcatcgg cgtgcagctc accgaagcat tggccgagta    4380
ctggcactcc cgagtgcgca gcgaactcaa gctgaacgac ggtggatctg tcgctgattt    4440
tgatccagaa gacaagacca agttcttcga cctggattac cgcggcgccc gcttctcctt    4500
tggttacggt tcttgccctg atctggaaga ccgcgcaaag ctggtggaat tgctcgagcc    4560
aggccgtatc ggcgtggagt tgtccgagga actccagctg cacccagagc agtccacaga    4620
cgcgtttgtg ctctaccacc cagaggcaaa gtactttaac gtctaacacc tttgagaggg    4680
aaaactttcc cgcacattgc agatcgtgcc actttaacta aggttgacgg catgattaag    4740
gcgattttct gggacatgga cggcacgatg gtggactctg agccacagtg gggcattgct    4800
acctacgagc tcagcgaagc catgggccgc gcctcaccc cggagctccg ggaactcacc    4860
gtcggctcga gcctgccgcg caccatgcgc ttatgcgcag agcacgcagg cattacattg    4920
agcgacgcgg actacgagcg ctaccgggct ggcatgttcg cccgggtcca tgagcttttc    4980
gacgaatccc tcgtcccaaa tccaggcgtc accgaactcc tgacagagtt gaaggccctc    5040
gagatcccca tgttggtcac caccaacaca gagcgcgatc tcgcgacccg ttcagtcgca    5100
```

```
gccgtgggaa atgagttctt catcggttct atcgctggtg atgaagtccc aacagcaaag    5160
ccagcccccg acatgtacct cgaagcagca cgacgtgtgg gctttgaccc atcagagtgc    5220
ctcgtgttcg aagattccta caacggcatg ctgggcgctg ttactgcagg ttgccgcgtc    5280
attggtctgc acccagaaga agtccaagcg ccagaaggtg tagtgccttt gcgttccctc    5340
cacggtaaaa actctttcga aggtgtcacc gctgagatgg tcactgcctg gtaccaccag    5400
atcgagccgg caggtgtcgc aaaataaaac caggtggggg agtgaaatta ttcgactaat    5460
atcctccccc aaacacacat tgataactgt tgtgtggaag aatgtaccga gtgaagacat    5520
ttgactcgct gtacgaagaa cttcttaacc gtgctcagac ccgccctgaa gggtctggaa    5580
ccgtggccgc cttggataaa ggcatccatc atctaggtaa aaggtcatc gaagaagccg    5640 gagaggtctg gattgcagcc gagtat                                         5666

<210> SEQ ID NO 27
<211> LENGTH: 3613
<212> TYPE: DNA
<213> ORGANISM: Corynebacterium glutamicum

<400> SEQUENCE: 27
tcctgtgggg tgaacttgac ctgtgctggg ccacgacgtc cgaaaacgtg cacttcagtg      60
gccttgtttt ctttgaggga gtcgtagacg ttgtcggaaa tttcggtgac tttgagctcg     120
tcgcctgtct tagccaggat gcgggctacg tcgaggccga cgttaccaac gccgataaca     180
gcgacggact gtgcagacag atcccaggag cgctcgaagc gtgggttgcc gtcgtagaag     240
ccaacgaact cgccggcacc gaaggagcct tctgcttcaa ttccggggat gttgaggtcg     300
cggtctgcaa ctgcgccggt ggagaacacg actgcatcgt agtagtcgcg gagttcttcg     360
acggtgatgt ctttgccgat ttcaatgtta ccgagcaggc gcaggcgtgg cttgtccaac     420
acgttgtgca gggacttaac gatgcccttg atgcgtgggt ggtctggagc aacgccgtaa     480
cggatgagtc cgaacggtgc aggcatttgc tcgaaaaggt caacgaacac ttcgcgctct     540
tcattgcgga tgaggaggtc ggatgcgtaa atgccagcag ggccagctcc gatgacggct     600
acgcgcaggg gagttgtcat gtgtttgaag ttgccttttcg tgagcccttt tatggaaaca     660
agggtgtgaa aatcaagtag ttaaaggtgt ttcaagtcca ggctgtttaa cactcctaga     720
ccgcttggtc tgtaaacgta gcagcgaaat gcgacaatgc gaagactttt gcttaattaa     780
attcaaactc catgaaaaaa ctagacagat cggtctatta tattcacggt gaacctaacc     840
taatatcccc aggttaattc atttaaacgg gcattaggtg actccattgc tttcagtctc     900
atgaatctaa tggttggtct agacagagcg gtacgtctaa gtttgcggat agatcaaacc     960
gagtgacatg tacttcacta gctctttaag gattaactcc ccatgacaac aaccaccgga    1020
agtgcccggc cagcacgtgc cgccaggaag cctaagcccg aaggccaatg gaaaatcgac    1080
ggcaccgagc gcttaaccac tgccgaggaa attaagcaag aagaacccgc ttttgctgtc    1140
aagcagcggg tcattgatat ttactccaag cagggttttt cttccattgc accggatgac    1200
attgccccac gctttaagtg gttgggcatt tacacccagc gtaagcagga tctgggcggt    1260
gaactgaccg gtcagcttcc tgatgatgag ctgcaggatg agtacttcat gatgcgtgtg    1320
cgttttgatg gcggactggc ttcccctgag cgcctgcgtg ccgtgggtga aatttctagg    1380
gattatgctc gttccaccgc ggacttcacc gaccgccaga acattcagct gcactggatt    1440
cgtattgaag atgtgcctgc gatctgggag aagctagaaa ccgtcggact gtccaccatg    1500
```

-continued

```
cttggttgcg gtgacgttcc acgtgttatc ttgggctccc cagtttctgg cgtagctgct      1560
gaagagctga tcgatgccac cccggctatc gatgcgattc gtgagcgcta cctagacaag      1620
gaagagttcc acaaccttcc tcgtaagttt aagactgcta tcactggcaa ccagcgccag      1680
gatgttaccc acgaaatcca ggacgtttcc ttcgttcctt cgattcaccc agaattcggc      1740
ccaggatttg agtgctttgt gggcggtggc ctgtccacca acccaatgct tgctcagcca      1800
cttggttctt ggattccact tgatgaggtt ccagaagtgt gggctggcgt cgccggaatt      1860
ttccgcgact acggcttccg acgcctgcgt aaccgtgctc gcctcaagtt cttggtggca      1920
cagtggggta ttgagaagtt ccgtgaagtt cttgagaccg aatacctcga gcgcaagctg      1980
atcgatggcc cagttgttac caccaaccct ggctaccgtg accacattgg cattcaccca      2040
caaaaggacg gcaagttcta cctcggtgtg aagccaaccg ttggacacac caccggtgag      2100
cagctcattg ccattgctga tgttgcagaa aagcacggca tcaccaggat tcgtaccacg      2160
gcggaaaagg aactgctctt cctcgatatt gagagaaaga accttactac cgttgcacgc      2220
gacctggatg aaatcggact gtactcttca ccttccgagt tccgccgcgg catcatttcc      2280
tgcaccggct tggagttctg caagcttgcg cacgcaacca ccaagtcacg agcaattgag      2340
cttgtcgacg aactggaaga gcgcctcggc gatttggatg ttcccatcaa gattgcactg      2400
aacggttgcc ctaactcttg tgcacgcacc caggtttccg acatcggatt caagggacag      2460
accgtcactg atgctgacgg caaccgcgtt gaaggtttcc aggttcacct gggcggttcc      2520
atgaacttgg atccaaactt cggacgcaag ctcaagggcc acaaggttat tgccgatgaa      2580
gtgggagagt acgtcactcg cgttgttacc cacttcaagg aacagcgcca cgaggacgag      2640
cacttccgcg attgggtcca gcgggccgct gaggaagatt tggtgtgagt cttcggagga      2700
aacccaatcc caaccgcaac caccctctgt actgcccata ctgcgcggga gaagttcttt      2760
tccccgatga gcaaacagaa ttcgcgtggt tgtgtgcgga ttgcaccaga gttttttgaag     2820 tgaaatatca cggccaggac gatccagtgc acaggccagc accagcaaag tccacatcgc      2880
aagcattaaa agaatctctc gaaagacaca aaagaggtga gtcgcaacaa tgagctttca      2940
actagttaac gccctgaaaa atactggttc ggtaaaagat cccgagatct cacccgaagg      3000
acctcgcacg accacaccgt tgtcaccaga ggtagcaaaa cataacgagg aactcgtcga      3060
aaagcatgct gctgcgttgt atgacgccag gcgcaagag atcctggaat ggacagccga      3120
gcacgcgccg ggcgctattg cagtgacctt gagcatggaa acaccgtgc tggcggagct      3180 ggctgcgcgg cacctgccgg aagctgatt cctcttttg acaccggtt accacttcaa       3240 ggagacccctt gaagttgccc gtcaggtaga tgagcgctat tcccagaagc ttgtcaccgc      3300
gctgccgatc ctcaagcgca cggagcagga ttccatttat ggtctcaacc tgtaccgcag      3360
caacccagcg gcgtgctgcc gaatgcgcaa agttgaaccg ctggcggcgt cgttaagccc      3420
atacgctggc tggatcaccg gcctgcgccg cgctgatggc ccaacccgtg ctcaagcccc      3480
tgcgctgagc ttggatgcca ccggcaggct caagatttct ccaattatca cctggtcatt      3540
ggaggaaacc aacgagttca ttgcggacaa caacctcatc gatcacccac ttacccatca      3600
gggttatcca tca                                                          3613
```

<210> SEQ ID NO 28
<211> LENGTH: 3311
<212> TYPE: DNA
<213> ORGANISM: Corynebacterium glutamicum

<400> SEQUENCE: 28

-continued

```
ctcattccag cgtcacgacg ttccgaaggt actggttacc tggcattggg cactaccgtt     60
tctgcagcac ttggaccagc cctagcactt tttgtcctag aacatttga ttacgacatg    120 ctgtttatcg tggtcttggc aacctcggtc atctctttga tcgccgtcgt gttcatgtac    180
tttaagacca gcgaccctga gccttctggg aaccagcca agttcagctt caaatctatt    240
atgaacccaa agatcatccc catcggcatc tttatcttgc ttatttgctt tgcttactct    300
ggcgtcattg cctacatcaa cgcatttgct gaagaacgcg atctgattac gggtgctgga    360
ttgttcttca ttgcctacgc agtatcaatg tttgtgatgc gcagcttcct tggcaaactg    420
caggaccgtc gcggagacaa cgtcgttatt tactttggat tgttcttctt cgttatttcc    480
ttgacgattt tgtcctttgc cacttccaac tggcacgttg tgttgtccgg agtcattgca    540
ggtctgggat acggcacttt gatgccagca gtgcagtcca tcgctgttgg tgtagtagac    600
aaaaccgaat tcggtacggc cttctccact tgttcctgt ttgtggactt aggttttggc    660
tttggaccta ttatcctggg agcagtttct gcggcaattg gtttcggacc tatgtatgca    720
gcactggcag gtgtgggtgt gattgccgga atcttctacc tgttcacaca cgctcgcacc    780
gatcgagcta agaatggctt tgttaaacac ccagagcctg tcgctttagt tagctagttc    840 tttcagctttt ccctcccgat cagcgtaaac cggcccttcc ggttttgggg tacatcacag    900
aacctgggct agcggtgtag acccgaaaat aaacgagcct tttgtcaggg ttaaggttta    960
ggtatctaag ctaaccaaac accaacaaaa ggctctaccc atgaagtcta ccggcaacat   1020
catcgctgac accatctgcc gcactgcgga actaggactc accatcaccg gcgcttccga   1080
tgcaggtgat tacaccctga tcgaagcaga cgcactcgac tacacctcca cctgcccaga   1140
atgctcccaa cctggggtgt ttcgtcatca cacccaccgg atgctcattg atttacccat   1200
cgtcgggttt cccaccaaac tgtttatccg tctacctcgc taccgctgca ccaacccac    1260 atgtaagcaa aagtatttcc aagcagaact aagctgcgct gaccacgta aaaaggtcac   1320 ccaccgggtc acccgctgga ttttacaacg ccttgctatt gaccggatga gtgttcacgc   1380
aaccgcgaaa gcacttgggc tagggtggga tttaacctgc caactagccc tcgatatgtg   1440
ccgtgagctg gtctataacg atcctcacca tcttgatgga gtgtatgtca ttggggtgga   1500
tgagcataag tggtcacata atagggctaa gcatggtgat gggtttgtca ccgtgattgt   1560
cgatatgacc gggcatcggt atgactcacg gtgtcctgcc cggttattag atgtcgtccc   1620
aggtcgtagt gctgatgctt tacggtcctg gcttggctcc cgcggtgaac agttccgcaa   1680
tcagatacgg atcgtgtcca tggatggatt ccaaggctac gccacagcaa gtaaagaact   1740
cattccttct gctcgtcgcg tgatggatcc attccatgtt gtgcggcttg ctggtgacaa   1800
gctcaccgcc tgccggcaac gcctccagcg ggagaaatac cagcgtcgtg gtttaagcca   1860
ggatccgttg tataaaaacc ggaagacctt gttgaccacg cacaagtggt tgagtcctcg   1920
tcagcaagaa agcttggagc agttgtgggc gtatgacaaa gactacgggg cgttaaagct   1980
tgcgtggctt gcgtatcagg cgattattga ttgttatcag atgggtaata agcgtgaagc   2040
gaagaagaaa atgcggacca ttattgatca gcttcgggtg ttgaagggc cgaataagga   2100 actcgcgcag ttgggtcgta gtttgtttaa acgacttggt gatgtgttgg cgtatttcga   2160
tgttggtgtc tccaacggtc cggtcgaagc gatcaacgga cggttggagc atttgcgtgg   2220
gattgctcta ggtttccgta atttgaacca ctacattctg cggtgcctta tccattcagg   2280
gcagttggtc cataagatca atgcactcta aaacaggaag agcccgtaaa cctctgacta   2340
```

| | | |
|---|---|---|
| gcgtcaccct ctgattaagg cgaccgcgga tttaagagca gaggctgcca cgagcgcatc | 2400 | |
| ttcacggctg tgtgttgtac taaaagtaca gcgcacagcc gttcgtgctt gatcctcctc | 2460 | |
| aagccccaac gccagcaaca catgggatac ctctccggaa ccacaggcag aaccagggga | 2520 | |
| gcacacaatg ccttggcgtt ccaattccag aagaacagtt tcagatccta tgctgtcgaa | 2580 | |
| gagaaaagat gcgtgtccat caatgcgcat cctaggatgt ccagtcaggt gtgctcccgg | 2640 | |
| gatagtgaga acttcctcga tgaattcgcc aagatctgga taggattccg ccctggccaa | 2700 | |
| ttccaaggca gtggcaaagg cgatagcccc cgcaacgttt ccgtgccac tacgccgccc | 2760 | |
| ttttcctgg ccgccgccat ggattaccgg ctccagggga agctttgacc ataacactcc | 2820 | |
| aatcccttta ggcgcaccga atttatgacc cgacaaactt aacgcgtcaa ctcccaagtc | 2880 | |
| aaaggttaaa tgtgcagctt gcactgcatc ggtgtgaaaa ggcgtactgc ttaccgccgc | 2940 | |
| caactcagct atcggctgaa tggttcccac ctcattgttg cataaccaa tgctgatcaa | 3000 | |
| tgtggtgtcc ggcctgactg ctttgcggag accctcgggg agatcagcc cagtgtgatc | 3060 | |
| gggggatagg taggtgatct cgaaatcatg aaacctttca agataagcag cagtttctag | 3120 | |
| gacactgtca tgctcgatcg gggtggtgat gaggtgccgg ccacgaggat tagctaagca | 3180 | |
| cgctcctttg atagcgaggt tgttggcttc tgatccaccc gacgtaaacg tcacctgtgt | 3240 | |
| ggggcgtcct ccgataatgc gggccacccg agttcgagca tcctccagcc ccgcagaggc | 3300 | |
| gagtcttccc a | 3311 | |

<210> SEQ ID NO 29
<211> LENGTH: 35
<212> TYPE: DNA
<213> ORGANISM: Artificial Sequence
<220> FEATURE:
<223> OTHER INFORMATION: primer

<400> SEQUENCE: 29
acccggggat cctctagaat gtttgtgatg cgcag           35

<210> SEQ ID NO 30
<211> LENGTH: 35
<212> TYPE: DNA
<213> ORGANISM: Artificial Sequence
<220> FEATURE:
<223> OTHER INFORMATION: primer

<400> SEQUENCE: 30
gtcagagagt acttacgctg atcgggaggg aaagc           35

<210> SEQ ID NO 31
<211> LENGTH: 35
<212> TYPE: DNA
<213> ORGANISM: Artificial Sequence
<220> FEATURE:
<223> OTHER INFORMATION: primer

<400> SEQUENCE: 31
atcagcgtaa gtactctctg actagcgtca ccctc           35

<210> SEQ ID NO 32
<211> LENGTH: 35
<212> TYPE: DNA
<213> ORGANISM: Artificial Sequence
<220> FEATURE:
<223> OTHER INFORMATION: primer

<400> SEQUENCE: 32
ctgcaggtcg actctagaaa agggattgga gtgtt                                35

<210> SEQ ID NO 33
<211> LENGTH: 35
<212> TYPE: DNA
<213> ORGANISM: Artificial Sequence
<220> FEATURE:
<223> OTHER INFORMATION: primer

<400> SEQUENCE: 33
caacgaaagg aaacaatgtc tacttcagtt acttc                                35

<210> SEQ ID NO 34
<211> LENGTH: 35
<212> TYPE: DNA
<213> ORGANISM: Artificial Sequence
<220> FEATURE:
<223> OTHER INFORMATION: primer

<400> SEQUENCE: 34
tagtcagaga gtgatttaga cgttaaagta ctttg                                35

<210> SEQ ID NO 35
<211> LENGTH: 35
<212> TYPE: DNA
<213> ORGANISM: Artificial Sequence
<220> FEATURE:
<223> OTHER INFORMATION: primer

<400> SEQUENCE: 35
atcaaaacag atatcatgac aacaaccacc ggaag                                35

<210> SEQ ID NO 36
<211> LENGTH: 35
<212> TYPE: DNA
<213> ORGANISM: Artificial Sequence
<220> FEATURE:
<223> OTHER INFORMATION: primer

<400> SEQUENCE: 36
cgctagtcag agagttcaca ccaaatcttc ctcag                                35

<210> SEQ ID NO 37
<211> LENGTH: 35
<212> TYPE: DNA
<213> ORGANISM: Artificial Sequence
<220> FEATURE:
<223> OTHER INFORMATION: primer

<400> SEQUENCE: 37
ccgatcagcg taagtagaaa catcccagcg ctact                                35

<210> SEQ ID NO 38
<211> LENGTH: 35
<212> TYPE: DNA
<213> ORGANISM: Artificial Sequence
<220> FEATURE:
<223> OTHER INFORMATION: primer

<400> SEQUENCE: 38
aactgaagta gacattgttt cctttcgttg ggtac                                35

<210> SEQ ID NO 39
<211> LENGTH: 35
<212> TYPE: DNA

```
<213> ORGANISM: Artificial Sequence
<220> FEATURE:
<223> OTHER INFORMATION: primer

<400> SEQUENCE: 39
tactttaacg tctaaggtac cggcgcttca tgtca                                35

<210> SEQ ID NO 40
<211> LENGTH: 35
<212> TYPE: DNA
<213> ORGANISM: Artificial Sequence
<220> FEATURE:
<223> OTHER INFORMATION: primer

<400> SEQUENCE: 40
ggtggttgtt gtcatgatat ctgttttgat ctcct                                35

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
atccccatcg gcatctttat                                                 20

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42
cgatcacact gggctgatct                                                 20

<210> SEQ ID NO 43
<211> LENGTH: 381
<212> TYPE: PRT
<213> ORGANISM: Corynebacterium glutamicum

<400> SEQUENCE: 43

Met Thr Leu Thr Phe His Trp Phe Leu Ser Thr Ser Gly Asp Ser Arg
1               5                   10                  15

Gly Ile Ile Gly Gly His Gly Ala Glu Lys Ser Gly Thr Ser Arg
            20                  25                  30

Glu Leu Ser His Ser Tyr Leu Lys Gln Leu Ala Leu Ala Glu Thr
        35                  40                  45

Asn Gly Phe Glu Ser Val Leu Thr Pro Thr Gly Thr Trp Cys Glu Asp
50                  55                  60

Ala Trp Ile Thr Asp Ala Ser Leu Ile Glu Ala Thr Lys Arg Leu Lys
65                  70                  75                  80

Phe Leu Val Ala Leu Arg Pro Gly Gln Ile Gly Pro Thr Leu Ser Ala
                85                  90                  95

Gln Met Ala Ser Thr Phe Gln Arg Leu Ser Gly Asn Arg Leu Leu Ile
            100                 105                 110

Asn Val Val Thr Gly Gly Glu Asp Ala Glu Gln Arg Ala Phe Gly Asp
        115                 120                 125

Phe Leu Asn Lys Glu Glu Arg Tyr Ala Arg Thr Gly Glu Phe Leu Asp
    130                 135                 140
```

-continued

```
Ile Val Ser Arg Leu Trp Arg Gly Glu Thr Val Thr His His Gly Glu
145                 150                 155                 160

His Leu Gln Val Glu Gln Ala Ser Leu Ala His Pro Pro Glu Ile Ile
                165                 170                 175

Pro Glu Ile Leu Phe Gly Gly Ser Ser Pro Ala Ala Gly Glu Val Ala
            180                 185                 190

Ala Arg Tyr Ala Asp Thr Tyr Leu Thr Trp Gly Glu Thr Pro Asp Gln
        195                 200                 205

Val Ala Gln Lys Ile Asn Trp Ile Asn Glu Leu Ala Ala Gln Arg Gly
    210                 215                 220

Arg Glu Leu Arg His Gly Ile Arg Phe His Val Ile Thr Arg Asp Thr
225                 230                 235                 240

Ser Glu Glu Ala Trp Val Val Ala Glu Lys Leu Ile Ser Gly Val Thr
                245                 250                 255

Pro Glu Gln Val Ala Lys Ala Gln Ala Gly Phe Ala Thr Ser Lys Ser
                260                 265                 270

Glu Gly Gln Arg Arg Met Ala Glu Leu His Ser Lys Gly Arg Ala Phe
            275                 280                 285

Thr Ser Gly Ser Thr Ala Arg Asp Leu Glu Val Tyr Pro Asn Val Trp
    290                 295                 300

Ala Gly Val Gly Leu Leu Arg Gly Gly Ala Gly Thr Ala Leu Val Gly
305                 310                 315                 320

Ser His Glu Glu Val Ala Asp Arg Ile Glu Glu Tyr Ala Ala Leu Gly
                325                 330                 335

Leu Asp Gln Phe Val Leu Ser Gly Tyr Pro Asn Leu Glu Glu Ala Phe
            340                 345                 350

His Phe Gly Glu Gly Val Ile Pro Glu Leu Leu Arg Arg Gly Val Asp
            355                 360                 365

Ile Lys Asn Gln Glu Ser Arg Val Leu Glu Pro Val Gly
    370                 375                 380
```